US012752018B2

(12) United States Patent
Tillement et al.

(10) Patent No.: US 12,752,018 B2
(45) Date of Patent: Oct. 6, 2026

(54) METHOD FOR TREATING TUMOURS BY CAPTURING COPPER AND/OR IRON

(71) Applicants: NH THERAGUIX, Meylan (FR); UNIVERSITE CLAUDE BERNARD LYON 1, Villeurbanne (FR); MEXBRAIN, Villeurbanne (FR); CENTRE NATIONAL DE LA RECHERCHE SCIENTIFIQUE—CNRS-, Paris (FR); INSERM (Institut National de la Santé et de la Recherche Médicale), Paris (FR); HOSPICES CIVILS DE LYON, Lyons (FR); INSTITUT NATIONAL DE RECHERCHE POUR L'AGRICULTURE, L'ALIMENTATION ET L'ENVIRONNEMENT, Paris (FR)

(72) Inventors: Olivier Tillement, Fontaines Saint-Martin (FR); François Lux, Lyons (FR); Delphine Vernos, Villeurbanne (FR); Claire Rodriguez-Lafrasse, Venissieux (FR); Thomas Brichart, Villeurbanne (FR); Marco Natuzzi, Lyons (FR); Alain Geloen, Lyons (FR); Simon Champagne, Lyons (FR); Matteo Martini, Villars les Dombes (FR); Paul Rocchi, Lyons (FR)

(73) Assignees: LYON INGENIERIE PROJECTS, Villeurbanne (FR); UNIVERSITE CLAUDE BERNARD LYON 1, Villeurbanne (FR); MEXBRAIN, Villeurbanne (FR); CENTRE NATIONAL DE LA RECHERCHE SCENTIFIQUE—CNRS, Paris (FR); INSERM (Institut National de la Santé de la Médicale), Paris (FR); HOSPICE CIVILS DE LYON, Lyons (FR); INSTITUT NATIONAL DE RECHERCHE POUR L'AGRICULTURE, L'ALIMENTATION ET L'ENVIRONNEMT, Paris (FR)

( * ) Notice: Subject to any disclaimer, the term of this patent is extended or adjusted under 35 U.S.C. 154(b) by 286 days.

(21) Appl. No.: 18/253,694

(22) PCT Filed: Nov. 19, 2021

(86) PCT No.: PCT/FR2021/052040
§ 371 (c)(1),
(2) Date: May 19, 2023

(87) PCT Pub. No.: WO2022/106787
PCT Pub. Date: May 27, 2022

(65) Prior Publication Data

US 2023/0346971 A1 Nov. 2, 2023

(30) Foreign Application Priority Data

Nov. 19, 2020 (FR) ...................................... 2011903

(51) Int. Cl.
*A61K 47/69* (2017.01)
*A61K 9/08* (2006.01)
(Continued)

(52) U.S. Cl.
CPC ........... *A61K 47/6935* (2017.08); *A61K 9/08* (2013.01); *A61N 5/10* (2013.01); *A61P 35/00* (2018.01); *A61N 2005/1098* (2013.01)

(58) Field of Classification Search
CPC .. A61K 47/6935; A61K 9/08; A61K 41/0038; A61K 47/547; A61K 47/59; A61K 49/128; A61K 49/1881; A61N 5/10; A61N 2005/1098; A61P 35/00; B82Y 5/00; B82Y 15/00
See application file for complete search history.

(56) References Cited

U.S. PATENT DOCUMENTS 5,208,324 A 5/1993 Klaveness et al.
10,987,435 B2 4/2021 Lux et al.
(Continued)

FOREIGN PATENT DOCUMENTS

WO WO 2019/008040 A1 1/2019
WO WO 2019/073182 A1 4/2019
WO WO 2019/122790 A1 6/2019

OTHER PUBLICATIONS

Machine translation for WO 2019/122790 A1; published Jun. 27, 2019.*
Zhou et al.; Biomaterials; 195 (2019); pp. 86-99. Published online Jan. 4, 2019.*
U.S. Appl. No. 17/998,708, filed Nov. 14, 2022 (371(c) Date), Lux et al.
U.S. Appl. No. 18/253,586, filed May 18, 2023 (371(c) Date), Tillement et al.
Mignot et al., Supporting Information for: "A Top-Down Synthesis Route to Ultrasmall Multifunctional Gd-Based Silica Nanoparticles for Theranostic Applications," Chemistry, A European Journal, 2013, 19, 6122-6136; retrieved on Sep. 29, 2023, from: https://chemistry-europe.onlinelibrary.wiley.com/doi/10.1002/chem.201203003, 6 pages.
(Continued)

*Primary Examiner* — Jeffrey T. Palenik
(74) *Attorney, Agent, or Firm* — Hoxie & Associates LLC

(57) ABSTRACT

The present disclosure relates to nanoparticles and the uses thereof in medicine, in particular in a method for treating cancer in a patient comprising in vivo capturing copper and/or iron in the patient by administering an effective amount of a colloidal solution of nanoparticles to said patient, and wherein the colloidal solution of nanoparticles is administered by intravenous, intratumoral or intrapulmonary injection, and wherein the nanoparticles have the following formula: $[Ch1]_n$—PS—$[Ch2]_m$, as described in the description.

11 Claims, 11 Drawing Sheets

(51) Int. Cl.
*A61N 5/10* (2006.01)
*A61P 35/00* (2006.01)

(56) References Cited

U.S. PATENT DOCUMENTS

| | | | | |
|---|---|---|---|---|
| 11,497,818 | B2 | 11/2022 | Lux et al. | |
| 11,512,003 | B2 | 11/2022 | Lux et al. | |
| 11,857,604 | B2 | 1/2024 | Tillement et al. | |
| 12,533,426 | B2 | 1/2026 | Lux et al. | |
| 2013/0195766 | A1 | 8/2013 | Lux et al. | |
| 2015/0050217 | A1 | 2/2015 | Cremillieux et al. | |
| 2016/0166706 | A1* | 6/2016 | Xu | A61K 47/59 424/78.17 |
| 2020/0289623 | A1 | 9/2020 | Tillement et al. | |
| 2021/0128730 | A1 | 5/2021 | Lux et al. | |
| 2021/0205213 | A1 | 7/2021 | Lux et al. | |
| 2022/0249711 | A1 | 8/2022 | Tillement et al. | |
| 2022/0288206 | A1 | 9/2022 | Timoshenko et al. | |
| 2023/0109283 | A1 | 4/2023 | Lux et al. | |
| 2023/0218781 | A1 | 7/2023 | Allouch et al. | |

OTHER PUBLICATIONS

Bouziotis et al., "$^{68}$Ga-radiolabeled AGuIX nanoparticles as dual-modality imaging agents for PET/MRI-guided radiation therapy," Nanomedicine (Lond.), 2017, 12 (13), 1561-1574.

Mignot et al., "A Top-Down Synthesis Route to Ultrasmall Multifunctional Gd-Based Silica Nanoparticles for Theranostic Applications," Chemistry, A European Journal, 2013, 19, 6122-6136.

Zhou et al., "Multifunctional nanoparticles based on a polymeric copper chelator for combination treatment of metastatic breast cancer," Biomaterials, 2019, 195, 86-99, Abstract Only.

U.S. Appl. No. 19/122,480, filed Apr. 18, 2025 (371(c) Date), Lux et al.

* cited by examiner

[Fig. 1]
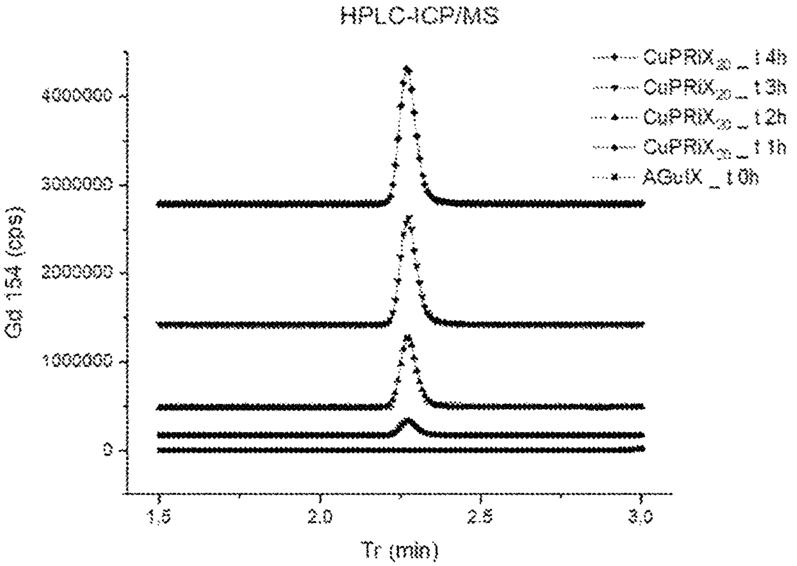
[Fig. 2]
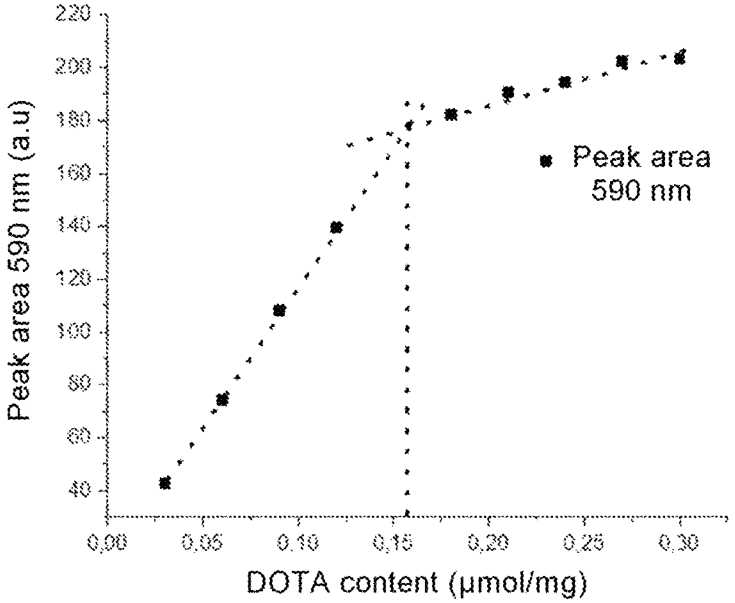

[Fig. 3]
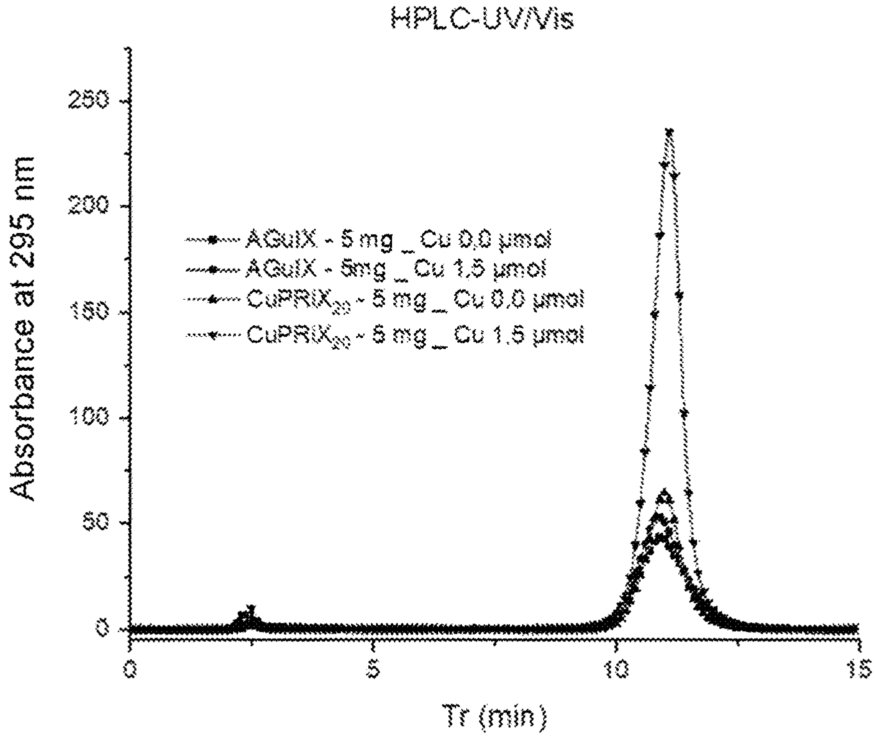

[Fig. 4]
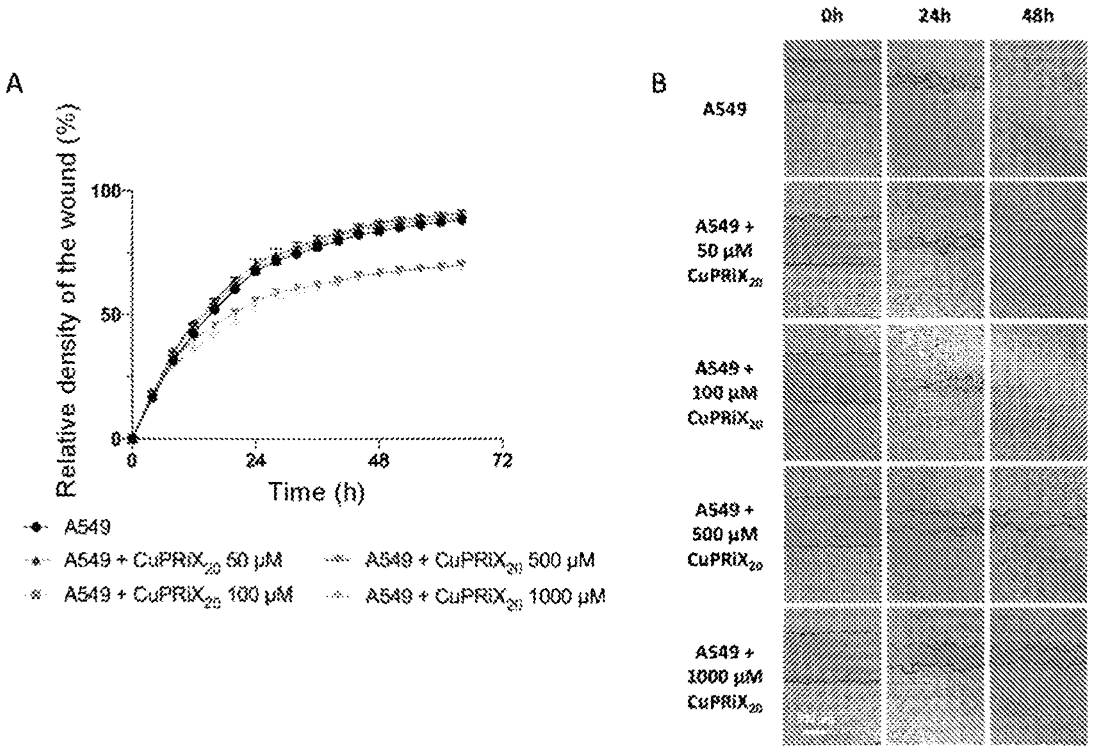

[Fig. 5]
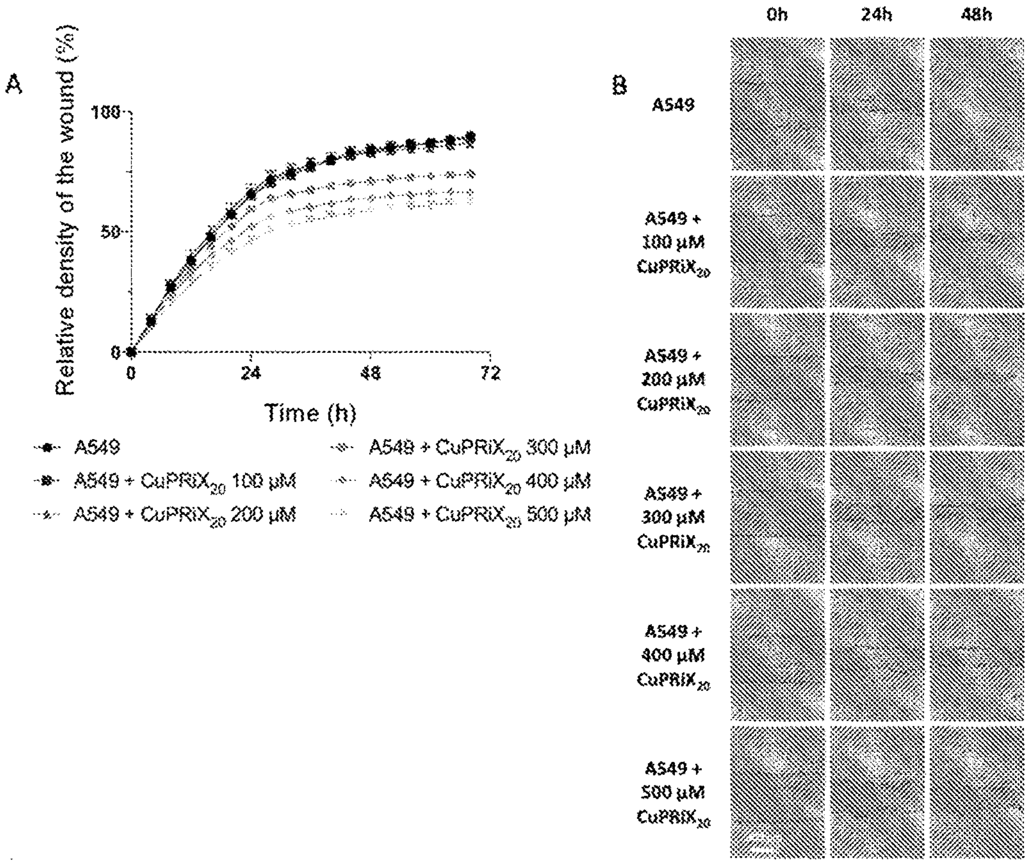

[Fig. 6]
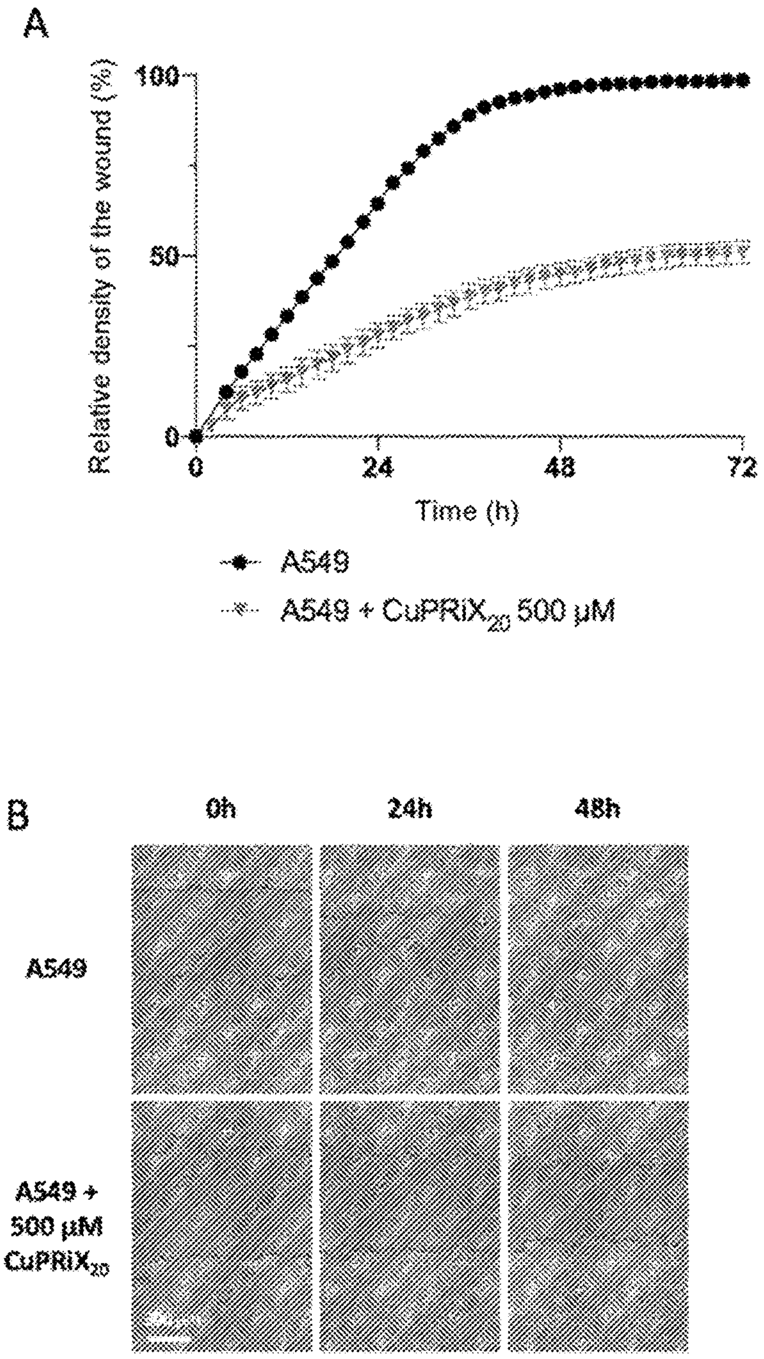

[Fig. 7]
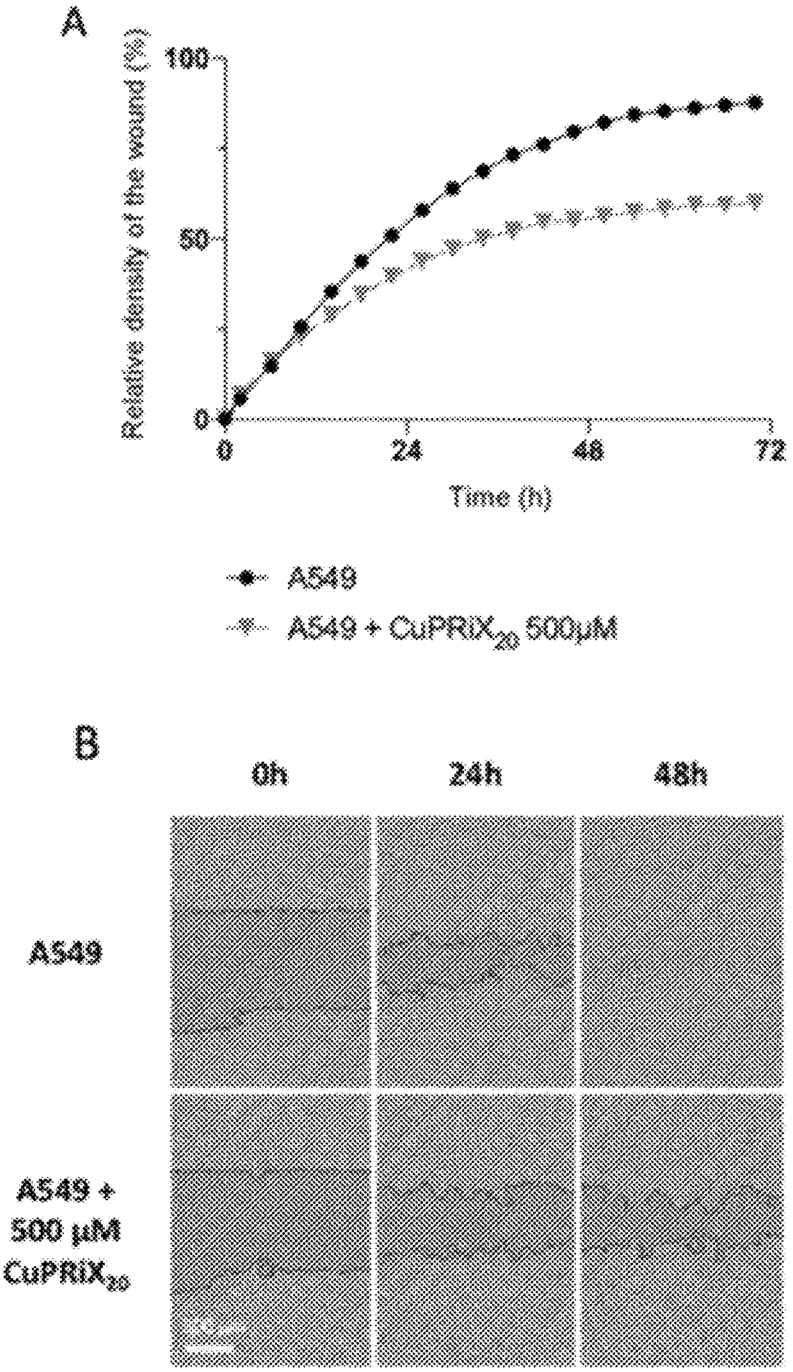

[Fig. 8]
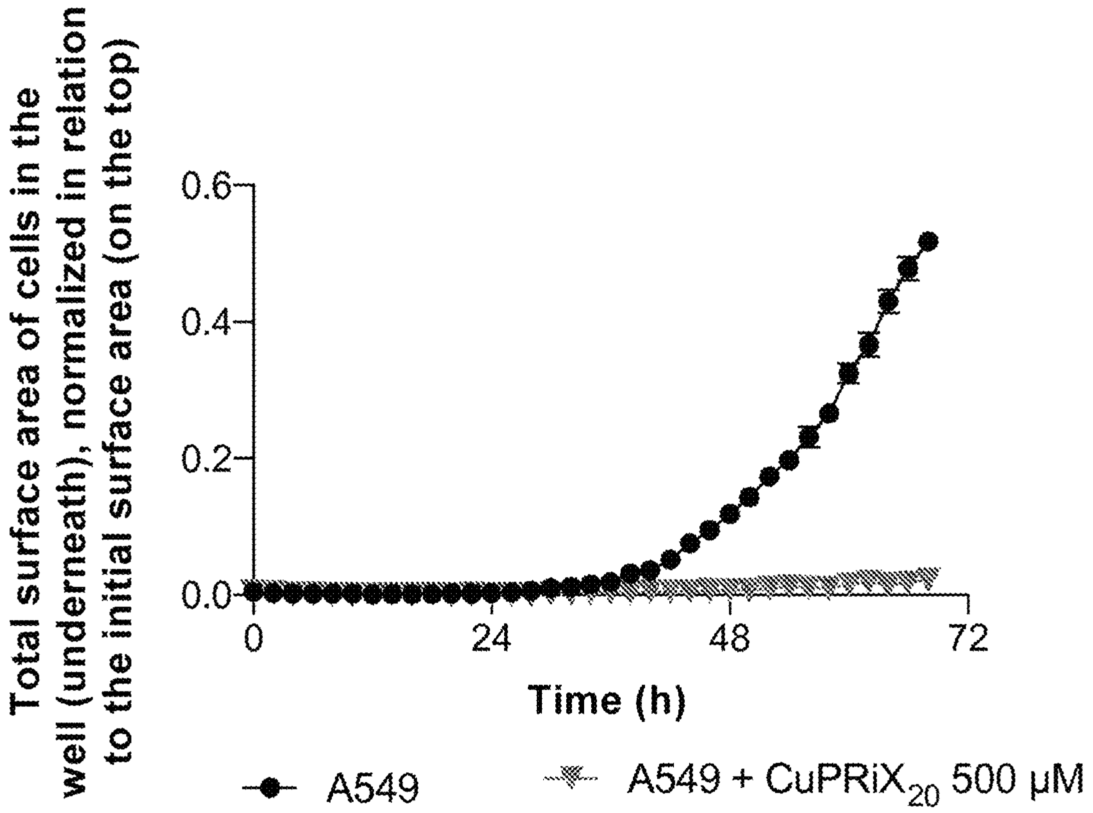

[Fig. 9]
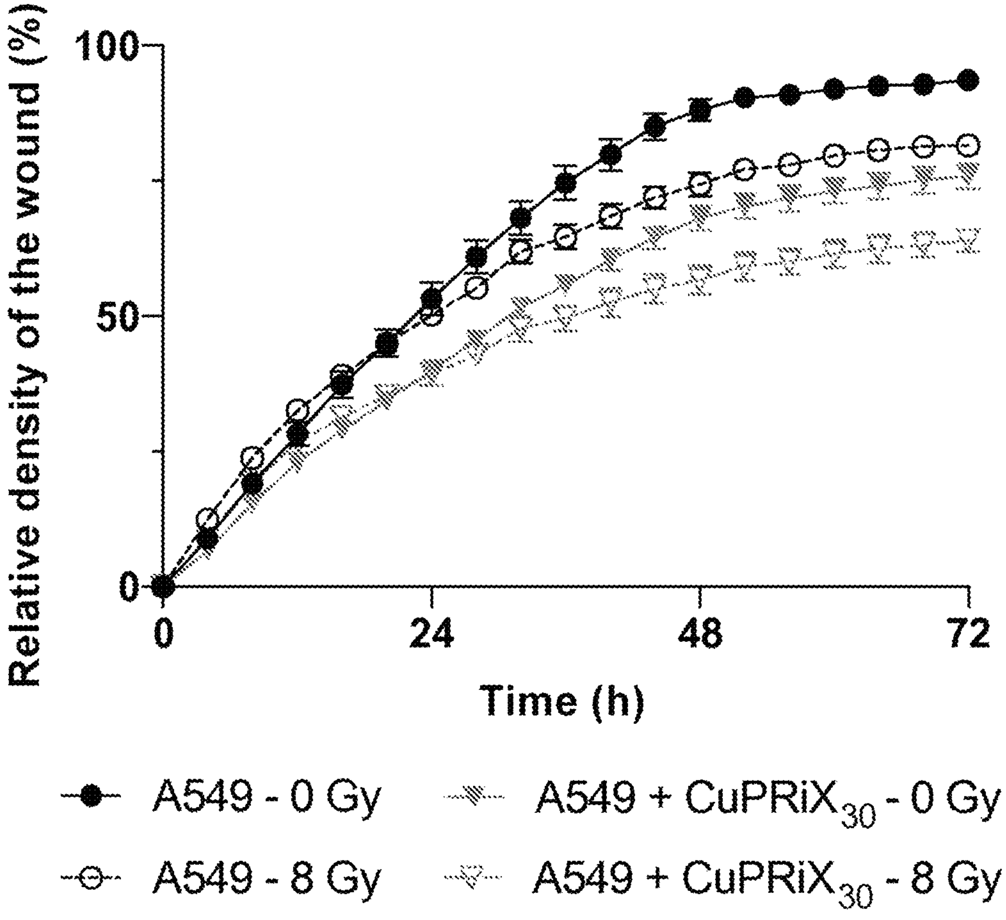

[Fig. 10]
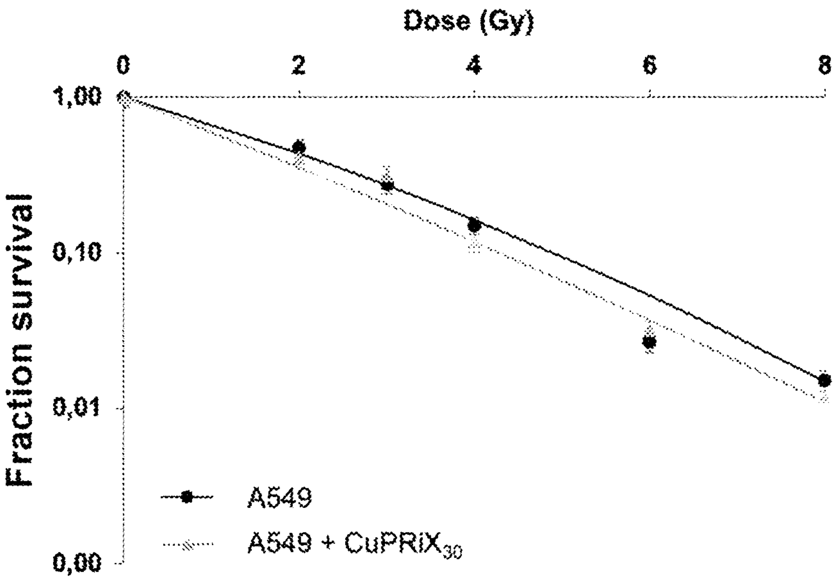
[Fig. 11]
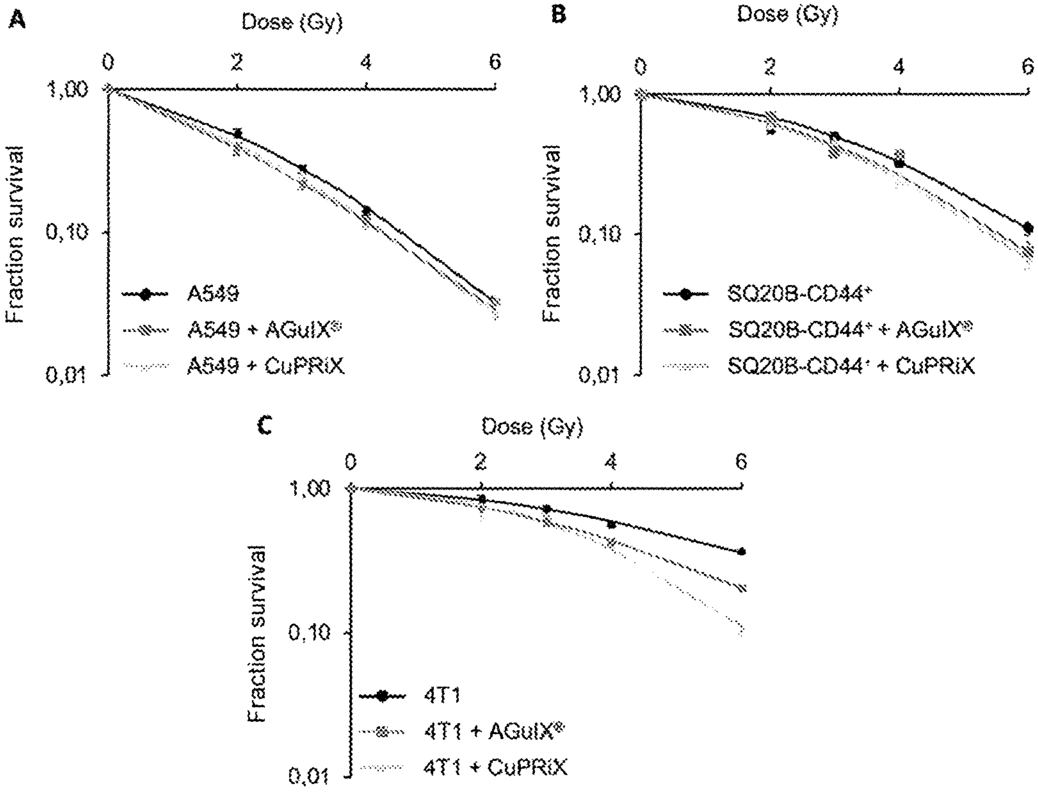

[Fig. 12]
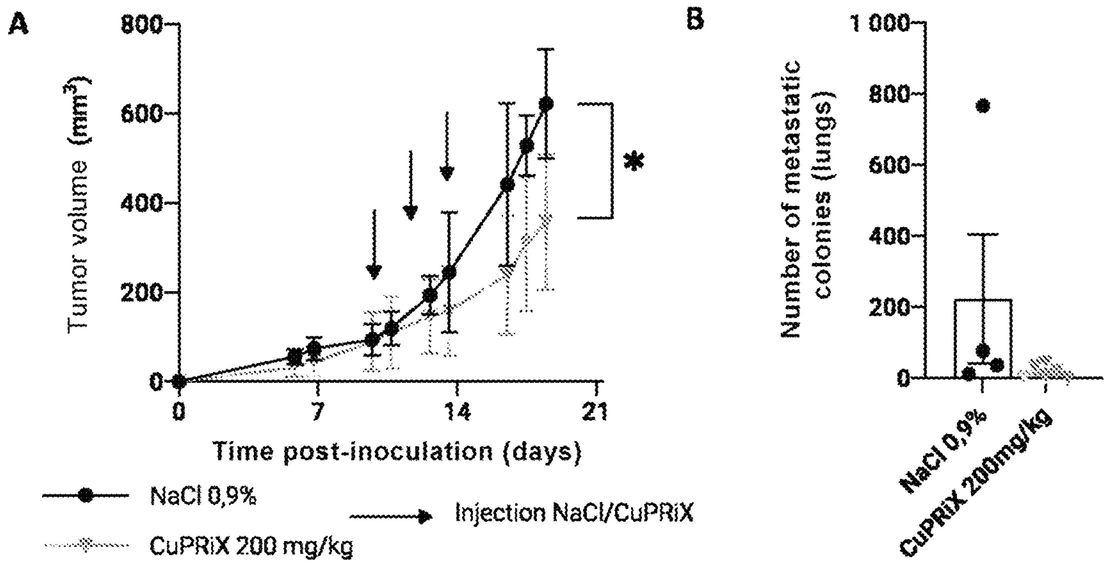

[Fig. 13]
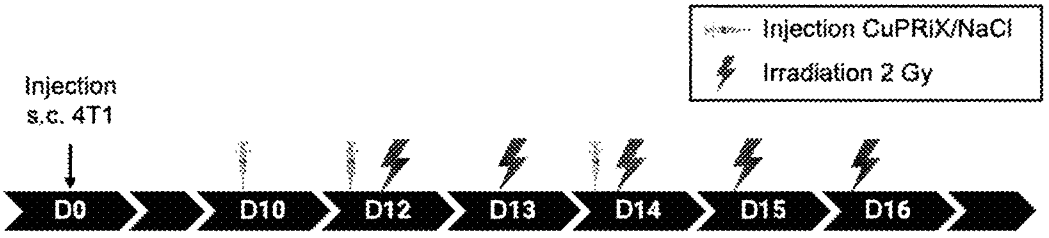
[Fig. 14]
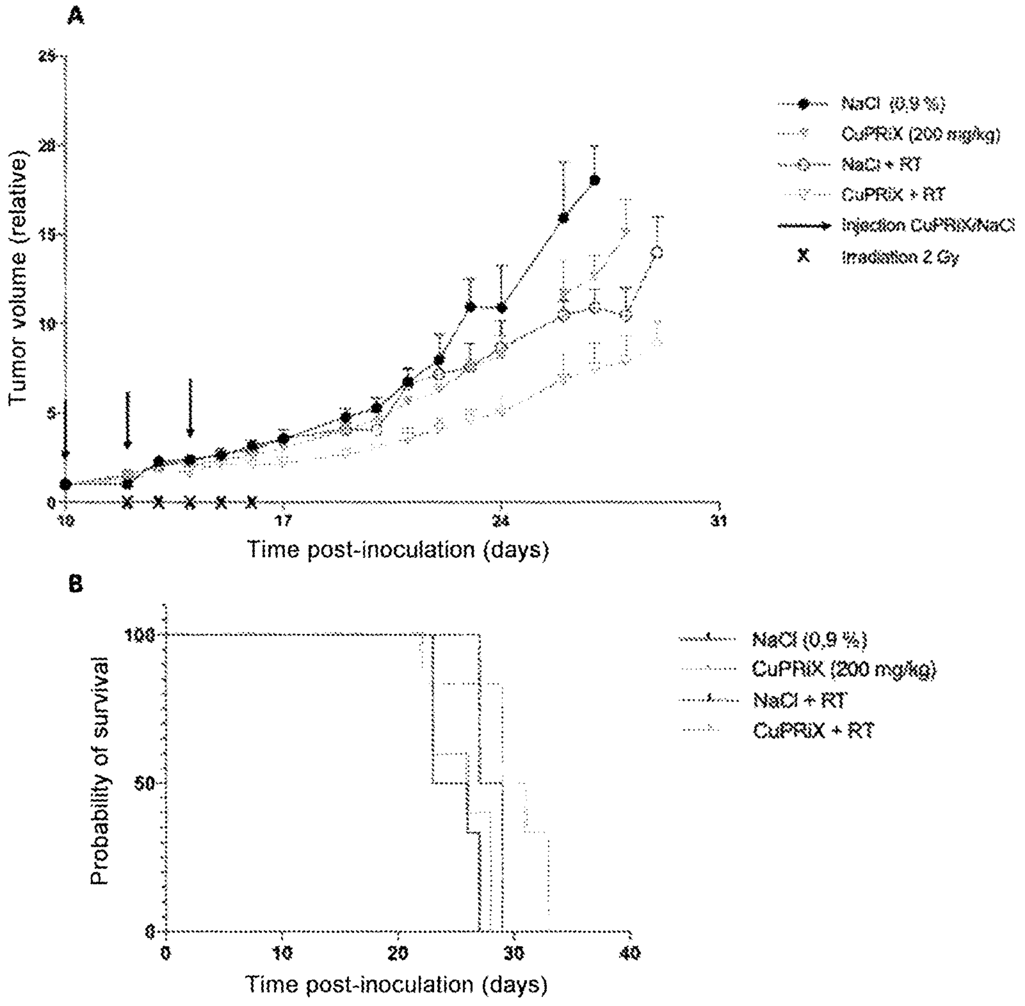

METHOD FOR TREATING TUMOURS BY CAPTURING COPPER AND/OR IRON

CROSS REFERENCE TO RELATED APPLICATIONS

This application is the National Stage Entry under 35 U.S.C. § 371 of International Application No. PCT/FR2021/052040 filed Nov. 19, 2021, which claims priority to French Patent Application No. 2011903 filed Nov. 19, 2020, the contents of each of which are hereby incorporated by reference in their entireties.

TECHNICAL FIELD

The present disclosure relates to nanoparticles and the uses thereof in the field of medicine, in particular for the treatment of tumors by capturing copper and/or iron.

PRIOR ART

Reducing the content of copper and/or iron in organisms is an interesting strategy in treating metastatic cancers. While this reduction can be offered by simple treatment regimens [Counter C M, Brady D C, Turski M L, & Thiele D J (2015) Methods of treating and preventing cancer by disrupting the binding of copper in the map-kinase pathway 1(19) 0-4], the concept focuses on administering medicaments that are able to complex copper. Several copper-chelating agents have been tested to date: penicillamine, trientine, disulfiram, clioquinol and tetramolybdate, and also iron-chelating agents which, as for copper, have been used to treat metal poisoning: deferoxamine (DFO), deferiprone (DFP), deferasirox (Gaur et al, Inorganics, 2018, 6, 126). Interesting preclinical and clinical results have been achieved, however they are often limited or associated with side effects that might prevent them from being used.

Copper and/or iron are metal cations that are essential to life; however, many other metal cations also are. Thus, the use of chelators that are too powerful risks weakening the patient in other parts of their body: this is a common problem when using the medicaments used in chemotherapy.

Conversely, the use of a chelator which is not specific enough and which therefore has a greater affinity for other bioessential metals such as zinc, or even manganese, can also lead to problematic side effects.

One aim of treatment strategies based on depletion of copper or iron is therefore to increase the chelation constant and the specificity for copper and/or iron to an ever-greater extent, in order to limit side effects while ensuring good efficacy. Another aim is to target the location of this extraction, and to highly precisely capture copper and/or iron in the tumor environment.

Tetrathiomolybdate, a copper chelator that is highly effective in vitro, has demonstrated an effect in particular on the suppression of angiogenesis and tumor growth, by inducing a reduction in accessible copper [Alvarez H M, Xue Y, Robinson C D, Canalizo-Hernández M A, Marvin R G, Kelly R A, Mondragón A, Penner-Hahn JE, & O'Halloran T V. (2010) Tetrathiomolybdate inhibits copper trafficking proteins through metal cluster formation Science (80-) 327 (5963) 331-334, https://doi.org/10.1126/science.1179907].

However, this use is still limited, and undesirable side effects such as erythema, optic neuritis, vomiting and leukopenia are observed during treatment, presumably associated with non-selective extraction of copper throughout the body.

Zhou et al proposed a combination of a chelator within polymers which assemble to form a capsule, making it possible to combine with another medicament (resiquimod-R848). The chelator used is TETA. The particles formed are larger in size (more than 400 kDa molecular weight of the RPTDH) and have a relatively limited capacity for extraction, the complexing agent being relatively specific for copper, but of low stability. Thus, a capacity for extraction of copper for contents of copper ions of greater than 50 μg/ml, i.e. 50 ppm, has been demonstrated (more than an order of magnitude higher than the natural concentration within our bodies). [Zhou P, Qin J, Zhou C, Wan G, Liu Y, Zhang M, Yang X, Zhang N, & Wang Y (2019) Multifunctional nanoparticles based on a polymeric copper chelator for combination treatment of metastatic breast cancer Biomaterials 195 86-99, https://doi.org/10.1016/j.biomaterials.2019.01.007]. In addition, in preclinical experiments, it was observed that, after injection, despite good targeting of the tumor by the particles, a significant proportion of the nanoparticles was found 6 h later in the liver, spleen, kidneys and lungs, and still in the lungs after 24 h.

Recently, Wu et al. proposed the used of copper-loaded nanoparticles to utilize the possibility of salting-out then capturing the copper, in order to initiate an anti-tumor effect [Wu W, Yu L, Jiang Q, Huo M, Lin H, Wang L, Chen Y, & Shi J (2019) Enhanced Tumor-Specific Disulfiram Chemotherapy by in Situ Cu2+ Chelation-Initiated Nontoxicity-to-Toxicity Transition *J Am Chem Soc* 141(29) 11531-11539, https://doi.org/10.1021/jacs.9b03503]. The size of these particles based on surface-pegylated mesoporous silica is approximately 165 nm. However, biodistribution studies of these large particles demonstrated a high degree of capture in the lungs, spleen, liver and heart. Aside from the original reversible aspect of the copper capture, the particles have a low capacity for chelating endogenous copper cations.

Feng et al. proposed the use of mesoporous copper sulfide particles loaded with a medicament known for its capacity for complexing copper (bleomycin). While this approach is beneficial due to the optical properties of copper sulfide for initiating absorption in the infrared range, it should nevertheless be borne in mind that the use of copper sulfide, even loaded by a complexing agent, risks introducing excessive amounts of copper into some regions. Also for this use, the particles are large in size (119.8 nm on average), in order to be able to encapsulate enough molecules. Feng Q, Zhang W, Li Y, Yang X, Hao Y, Zhang H, Li W, Hou L, & Zhang Z (2017) An intelligent NIR-responsive chelate copper-based anticancer nanoplatform for synergistic tumor targeted chemo-phototherapy*Nanoscale* 9(40) 15685-15695, https://doi.org/10.1039/c7nr05003h.

Deferoxamine (DFO), which is also used for treating iron metal poisoning, was the first chelator used in oncology for treatment by iron sequestration. Thus, DFO gave promising results for treating leukemia and neuroblastoma in preliminary clinical trials (Wang et al., Iron and Leukemia, 2019, 38, 406).

However, the use of these molecular chelates is limited by their rapid elimination, the lack of targeting the tumor, their toxicity at high doses, and the side effects that they cause.

In order to overcome these various problems, a number of teams have proposed combining iron chelators with nanoparticles or using nanoparticles that intrinsically chelate iron. Thus, J. Perring et al (Journal of Materials Science: Materials in medicine 2018, 29, 181) proposed forming nanoparticles of melanin, which naturally chelates iron. These particles are close to 220 nm in size and have demonstrated their capacity to capture iron and to lead to cancer cell death (rhabdomyosarcoma and glioblastoma). However, the large size of the nanoparticles risks inducing biodistribution that is not well suited to clinical use.

Conventional liposome-based drug delivery systems have also been proposed in order to improve the biodistribution of DFO. This was proposed by Lang et al (ACS Nano, 2019, 13, 2176-2189). They also combined DFO, within this liposome, with an HIF1α (hypoxia-inducible factor 1α) inhibitor in order to limit overexpression of HIF1α, which is usually observed with DFO. Encapsulation within liposomes made it possible to obtain nanoparticles of approximately one hundred nanometers. Preclinical trials in vitro and in vivo in rodent models made it possible to demonstrate anti-tumor action. Nevertheless, due to the size of the nanoparticles, a high degree of accumulation in the liver and spleen was observed.

Following the same reasoning, M. Theerasilp et al. (RSC Advances, 2017, 7, 11158) proposed the encapsulation of a different iron chelator within polymeric micelles. These micelles are formed from polymers having a hydrophobic portion, to form the core of the micelle, and a hydrophilic portion to provide colloidal stability. These micelles demonstrated anti-cancer activity in different cell lines, are approximately 25 nm in size, and exhibited salting-out based on the chelator and based on the pH.

It is clear from all these studies that, at the present time, there are no solutions which enable both effective and specific targeting of tumors, and sufficient local chelation of endogenous copper and/or iron for use in the treatment of tumors, in particular by administering nanoparticles in effective concentrations in the approximate mg/l range.

Another aim of the present disclosure is to provide a compound that enables copper and/or iron to be captured not only as it circulates generally in the blood, but also more specifically within tumor environments. In particular, one aim of the present disclosure is to provide a compound that makes it possible to capture, in the tumor environment, more than 10 μmol of copper and/or iron, or even more than 100 μmol of copper and/or iron per liter, i.e. to locally capture from 100 to 10 000 ppb of copper or iron.

Another aim of the present disclosure is to provide a compound that enables chelation with a high degree of specificity for copper and/or iron and a sufficiently long residence time in the tumor environments, in particular of several days or even several weeks.

Another aim of the present disclosure is to be able to locally release ions which would replace the copper and/or iron in the body, thereby neutralizing the effect thereof.

Another aim of the present disclosure is to provide a compound that is sufficiently small and makes it possible to target numerous solid tumors, including metastases, and in particular bone metastases.

Another aim of the present disclosure is to provide a compound that makes it possible both to capture copper and/or iron in tumors and to provide a radiosensitizing effect for treatment by radiotherapy. Thus, during irradiation, the localized capture of biometals should disrupt cell repair mechanisms and amplify the effects of the radiotherapy.

The present disclosure improves the situation with regard to one or more of these abovementioned aims.

Indeed, the use of chelating nanoparticles having suitable biodistribution and thermodynamic and kinetic properties that are suitable for treatment of tumors, in particular of primary and/or metastatic tumors, is proposed.

According to a first aspect, a nanoparticle of the following formula is proposed:

$$[Ch1]_n\text{—}PS\text{—}[Ch2]_m,$$

wherein:

PS is an organic or inorganic polymer matrix,

Ch1 is a chelating group which is uncomplexed or is complexed with a metal cation M1, M1 is absent, or selected from metal cations for which the constant for complex formation with Ch1 is less than that of copper and/or of iron, in particular at least ten times less; for example, M1 is selected from zinc or alkaline-earth metals, in particular calcium or magnesium, Ch2 is a chelating group, identical to or different from the chelating group Ch1, and complexed with a metal cation M2 having a high atomic number Z, greater than 40, and preferably greater than 50, characterized in that (i) the chelating groups Ch1 and Ch2 are grafted to the polymer matrix PS, (ii) the n/(n+m) ratio is between 10% and 100%, preferably between 40% and 60%, and (iii) the mean hydrodynamic diameter of the nanoparticle is between 1 and 50 nm, preferably between 2 and 20 nm, and more preferentially between 2 and 8 nm.

According to another aspect, a colloidal solution of nanoparticles as defined above is proposed.

According to another aspect, a pharmaceutical composition comprising said colloidal solution of nanoparticles and one or more pharmaceutically acceptable excipients is proposed.

The characteristics set out in the following paragraphs can optionally be implemented. They may be implemented independently or in combination with one another:

In one embodiment, the chelating group Ch1 is selected from those having a complex formation constant, in relation to copper(II), of greater than $10^{15}$.

In one embodiment, the chelating group Ch1 is selected from those having a constant for complex formation with copper(II) that is at least 10 times greater than their constant for complex formation with zinc and at least 106 times greater than their constants for complex formation with magnesium and calcium.

In another embodiment, the chelating group Ch1 is selected from those having a constant for complex formation with iron(II) that is at least 10 times greater than their constant for complex formation with zinc and at least $10^6$ times greater than their constants for the formation of complexes with magnesium and calcium.

In one embodiment, at least 50% of the Ch1 is complexed with a metal cation selected from the alkaline-earth metals.

In one embodiment, at least 50% of the Ch1 is complexed with zinc, calcium or magnesium.

In one embodiment, the chelating group Ch1, and where appropriate Ch2, is selected from macrocyclic agents, preferably from 1,4,7-triazacyclononanetriacetic acid (NOTA), 1,4,7,10-tetraazacyclododecane--tetraacetic acid (DOTA), 1,4,7-triazacyclononane-1-glutaric-4,7-diacetic acid (NODAGA), and 1,4,7,10-tetraazacyclododecane,1-(glutaric acid)-4,7,10-triacetic acid (DOTAGA), 2,2',2",2"'-(1,4,7,10-tetraazacyclododecane-1,4,7,10-tetrayl)tetraacetamide (DOTAM), and 1,4,8,11-tetraazacyclotetradecane (Cyclam), 1,4,7,10-tetraazacyclododecane (Cyclen) and deferoxamine (DFO) or another iron-chelating agent.

In one embodiment, the chelating group Ch1 is DOTAGA of the following formula (I) [Chem. 1]

(I)

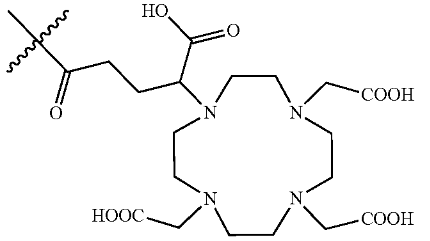

In one embodiment, PS is a polysiloxane matrix.

In one embodiment, the nanoparticle is characterized in that the weight ratio of silicon to the total weight of the nanoparticle is between 5% and 25%, the total number n+m of chelating groups grafted to the polymer is between 5 and 50 per nanoparticle, preferably between 10 and 30, and the nanoparticle has a mean diameter of between 2 and 8 nm.

In one embodiment, the nanoparticle is functionalized with a targeting agent, in particular a peptide, an immunoglobulin, a nanobody, an antibody, an aptamer or a targeting protein.

In one embodiment, the metal cation M2 is selected from radiosensitizers and/or magnetic resonance imaging contrast agents, in particular gadolinium or bismuth.

In one embodiment, the nanoparticle is characterized in that (i) PS is a polysiloxane matrix, (ii) Ch1 and Ch2 are DOTAGA chelating groups of the following formula (I) [Chem. 1]

(I)

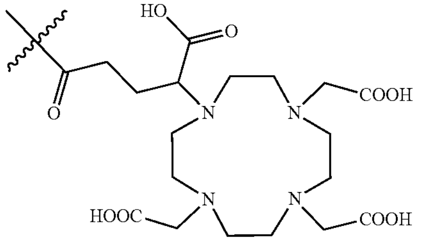

grafted to the polysiloxane matrix by covalent bonding, (iii) M1 is absent, and M2 is the gadolinium cation $Gd^{3+}$, (iv) n+m is between 5 and 50, preferably between 10 and 30, and (v) the mean hydrodynamic diameter is between 2 and 8 nm.

In one embodiment, the pharmaceutical composition is characterized in that it is an injectable composition for intravenous, intratumoral or intrapulmonary administration in a subject, in particular comprising an effective amount of chelating group Ch1 for the in vivo capture of copper and/or of iron in a tumor, the free chelator being for example at a concentration of at least 10 mM in the composition.

In one embodiment, the present disclosure provides a pharmaceutical composition, for use thereof in the treatment of cancer in a subject, in particular for the in vivo capture of copper and/or iron in a tumor. In particular, in this embodiment, said pharmaceutical composition may comprise an effective amount of metal cation M2, preferably gadolinium, for use as a radiosensitizer, and subject is treated by radiotherapy after administering said composition.

BRIEF DESCRIPTION OF THE DRAWINGS

Other features, details and advantages will become apparent upon reading the following detailed description and upon examining the appended drawings, in which:

FIG. 1 shows an HPLC-ICP/MS chromatogram of the free gadolinium in the reaction medium as a function of retention time, Tr, in minutes.

FIG. 2 shows the results of the titration of the free DOTA of CuPRiX$_{20}$ by measuring the luminescence intensity at 590 nm as a function of the amount of europium added per mg of CuPRiX$_{20}$ (excitation at 395 nm).

FIG. 3 is a chromatogram of AGuIX® and CuPRiX$_{20}$ before and after copper complexation.

FIG. 4 shows the effect of increasing concentrations of CuPRiX$_{20}$ (0, 50, 100, 500, 1000 μM of free chelate, equivalent to approximately 0, 150, 300, 600, 900, 1200, 1500 and 3000 μM of gadolinium) on the cell motility of A549 cells. (A) Quantitative analysis of wound closure as a function of time. The relative density of the wound is a measure of the density of the region of the wound relative to the density of the region.

FIG. 5 shows the effect of increasing concentrations of CuPRiX$_{20}$ (0, 100, 200, 300, 400 and 500 μM of free chelate, equivalent to approximately 0, 300, 600, 900, 1200, and 1500 μM of gadolinium) on the cell motility of A549 cells. (A) Quantitative analysis of wound closure as a function of time. The relative density of the wound is a measure of the density of the region of the wound relative to the density of the cellular region (%). The data is presented as mean ±SEM (n=6). (B) Images showing each condition, depicting the original wound and the wound 24 h and 48 h later. The scale bar indicates 300 μm.

FIG. 6 shows the effect of CuPRiX$_{20}$ (0 and 500 μM of free chelate, equivalent to approximately 0 and 1500 μM of gadolinium) on the cell motility of A549 cells. The cells were treated for 72 h with CuPRiX$_{20}$ before the wound was made. (A) Quantitative analysis of wound closure as a function of time. The relative density of the wound is a measure of the density of the region of the wound relative to the density of the cellular region (%). The data is presented as mean ±SEM (n=6). (B) Images showing each condition, depicting the original wound and the wound 24 h and 48 h later. The scale bar indicates 300 μm.

FIG. 7 shows the effect of CuPRiX20 (0 and 500 μM of free chelate, equivalent to approximately 0 and 1500 μM of gadolinium) on the cellular invasion of A549 cells. (A) Quantitative analysis of wound closure as a function of time. The relative density of the wound is a measure of the density of the region of the wound relative to the density of the cellular region (%). The data is presented as mean ±SEM (n=6). (B) Images showing each condition, depicting the original wound and the wound 24 h and 48 h later. The scale bar indicates 300 μm.

FIG. 8 shows the effect of CuPRiX20 on the chemotactic migration of A549 cells. Migration is expressed as the ratio of the confluence of cells that have crossed the membrane to the initial cell confluence seeded on the membrane. The data is presented as mean ±SEM (n=5).

FIG. 9 shows the effect of the combination of CuPRiX30 and photon irradiation on the motility of A549 cells. The relative density of the wound is a measure of the density of the region of the wound relative to the density of the cellular region (%). The data is presented as mean ±SEM (n=6).

FIG. 10 shows the radiosensitizing effect of CuPRiX30 in A549 cells.

FIG. 11 shows the radiosensitizing effect of CuPRiX and AGuIX on cell lines (A) A549, (B) SQ20B-CD44$^+$ and (C) 4T1.

FIG. 12 shows the efficacy of $CuPRiX_{30}$ in a triple-negative breast cancer mouse model on (A) tumor growth and (B) metastasis formation. (A) tumor growth is expressed as tumor volume ($1/2*L*W^2$, where L is the tumor length and W is the tumor width) as a function of time. The data is presented as mean ±SD,*p=0.038. AUC comparison: Kruskal-Wallis test. (B) Number of colonies from the lungs, by treatment group. NaCl n=4, $CuPRiX_{30}$ n=6.

FIG. 13 shows a diagram of injections and irradiations.

FIG. 14 shows the efficacy of a radiotherapy on tumor growth and survival.

DESCRIPTION OF THE EMBODIMENTS

The drawings and the description below substantially contain elements of a definite nature. They will therefore serve not only to better understand the present disclosure, but also to contribute to the definition thereof, where appropriate.

Nanoparticles

The present disclosure thus relates to nanoparticle of the following formula:

$$[Ch1]_n—PS—[Ch2]_m,$$

wherein:

PS is an organic or inorganic polymer matrix,

Ch1 is a chelating group which is uncomplexed or is complexed with a metal cation M1, M1 is absent, or selected from metal cations for which the constant for complex formation with Ch1 is less than that of copper and/or of iron, in particular at least ten times less; for example, M1 is selected from zinc or alkaline-earth metals, in particular calcium or magnesium, Ch2 is a chelating group, identical to or different from the chelating group Ch1, and complexed with a metal cation M2 having a high atomic number Z, greater than 40, and preferably greater than 50, characterized in that (i) the chelating groups Ch1 and Ch2 are grafted to the polymer matrix PS, (ii) the n/(n+m) ratio is between 10% and 100%, preferably between 40% and 60%, and (iii) the mean hydrodynamic diameter of the nanoparticle is between 1 and 50 nm, preferably between 2 and 20 nm, and more preferentially between 2 and 8 nm.

The nanoparticles according to the present disclosure are advantageously particles of a size in the nanometer range. In particular, the nanoparticles are small enough to target tumor cells using the EPR effect via the vascular system and to be rapidly eliminated renally, after intravenous administration of said nanoparticles.

According to the present disclosure, use will preferentially be made of nanoparticles having a very small diameter, for example of between 1 and 10 nm, preferably between 2 and 8 nm.

The size distribution of the nanoparticles is for example measured using a commercially available particle size analyzer, such as a Malvern Zetasizer Nano-S, based on PCS (Photon Correlation Spectroscopy). This distribution is characterized by a mean hydrodynamic diameter.

For the purposes of the invention, the "diameter" of the nanoparticles thus means the mean hydrodynamic diameter, i.e. the harmonic mean of the diameters of the particles. A method for measuring this parameter is also described in standard ISO 13321:1996.

The nanoparticles according to the present disclosure are nanoparticles comprising an organic or inorganic polymer matrix PS.

In some embodiments, the polymer of the matrix PS is selected from biocompatible polymers such as polyethylene glycol, polyethylene oxide, polyacrylamide, biopolymers, polysaccharides or polysiloxanes or mixtures thereof; preferably, the polymer PS is a polysiloxane.

"Nanoparticles comprising a polysiloxane polymer matrix" means in particular nanoparticles characterized by a percentage by weight of silicon of at least 5%, for example between 5 and 20% of the total weight of the nanoparticle.

"Polysiloxane" denotes an inorganic crosslinked polymer consisting of a chain of siloxanes. The structural units of the polysiloxane, which are identical or different, are of the following formula: Si(OSi)nR4—n, wherein R is an organic molecule bonded to the silicon via a covalent Si-C bond n is an integer of between 1 and 4.

By way of a preferred example, the term "polysiloxane" encompasses in particular polymers resulting from the condensation, by the sol-gel process, of tetraethylorthosilicate (TEOS) and aminopropyltriethoxysilane (APTES).

For the purposes of the present disclosure, "chelating group" means an organic group that is able to complex a metal cation. Preferably, said chelating groups above are directly or indirectly bonded, via covalent bonding, to the silicons of the polysiloxanes of the matrix PS of the nanoparticles. "Indirect" bonding means the presence of a "linker" or "spacer" molecule between the nanoparticle and the chelating group, said linker or spacer being covalently bonded to one of the constituents of the nanoparticle.

The particular role of the chelating group Ch1 is to capture endogenous copper or endogenous iron. In one embodiment, in order to enable the in vivo capture of copper, a chelating group Ch1 will advantageously be selected from those having a complex formation constant, in relation to copper(II), of greater than $10^{15}$, for example greater than $10^{20}$.

In one embodiment, in order to enable the in vivo capture of iron, a chelating group Ch1 will advantageously be selected from those having a complex formation constant, in relation to iron(II), of greater than $10^{15}$, for example greater than $10^{20}$.

In one embodiment, the chelating group Ch1 is free, or complexed (at least in part) with a metal cation M1. In this case, the metal cation M1 is complexed with a chelating group carefully selected to enable the in vivo transmetalation of the metal cation M1 with copper and/or iron. Thus, in a specific embodiment, the chelating group Ch1 is advantageously selected from those having a constant for complex formation with copper(II) or iron that is at least 10 times greater than their constant for complex formation with zinc and at least $10^6$ times greater than their constants for complex formation with magnesium and calcium.

The chelating group Ch1 can be obtained by the grafting (covalent bonding), onto the nanoparticle, of macrocyclic agents, preferably selected from DOTA (1,4,7,10-tetraazacyclododecane-N,N',N",N'"-tetraacetic acid), NOTA (1,4,7-triazacyclononane-1,4,7-triacetic acid), NODAGA (1,4,7-triazacyclononane-1-glutaric acid-4,7-diacetic acid), DOTAGA (2-(4,7,10-tris(carboxymethyl)-1,4,7,10-tetraazacyclododecan-1-yl)pentanedioic acid), DOTAM (1,4,7,10-tetrakis(carbamoylmethyl)-1,4,7,10-tetraazacyclododecane) and 1,4,8,11-tetraazacyclotetradecane (Cyclam), 1,4,7,10-tetraazacyclododecane (Cyclen), deferoxamine. Deferoxamine is more particularly beneficial with a view to iron capture.

In one embodiment, in particular in the embodiments described in the two preceding paragraphs, the metal cation M1 complexed with the chelating group Ch1 is selected from zinc or alkaline-earth metals, in particular magnesium or calcium. Preferably, at least 50%, 60%, 70%, 80%, or even at least 90% of the Ch1 is complexed with zinc, calcium, magnesium or another alkaline-earth metal.

In a preferred embodiment, the chelating group Ch1 is DOTAGA of the following formula (I) [Chem. 1]

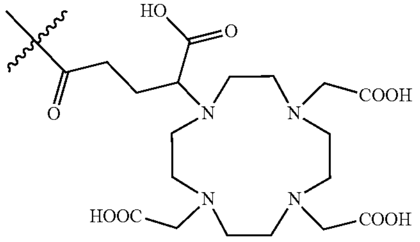

(I)

According to the present disclosure, the chelating group Ch2, which is identical to or different from Ch1, is complexed with a metal cation M2 having a high atomic number Z, greater than 40, and preferably greater than 50. Thus, a nanoparticle comprises, grafted to the polymer matrix PS, one or more groups Ch1, which are complexed or uncomplexed with a metal cation M1, for example zinc, magnesium, calcium or other alkaline-earth metals, and one or more groups Ch2, which are complexed with a metal cation M2 having a high atomic number Z, greater than 40.

The chelating group Ch2 is thus preferably selected from chelating groups for which the constant of complex formation with the metal cation M2 is greater than $10^{15}$, or even greater than $10^{20}$. In a particular embodiment, the metal cations M2 are selected from those which make it possible to use said nanoparticle as a radiosensitizer.

For the purposes of the present disclosure, "radiosensitizer" means a compound that makes it possible to make cancer cells more sensitive to the radiation used in radiotherapy.

The chelating group Ch2, which is identical to or different from Ch1, can also be selected from macrocyclic agents, and preferably from DOTA (1,4,7,10-tetraazacyclododecane-N, N', N'', N'''-tetraacetic acid), NOTA (1,4,7-triazacyclononane-1,4,7-triacetic acid), NODAGA (1,4,7-triazacyclononane-1-glutaric acid-4,7-diacetic acid), DOTAGA (2-(4,7,10-tris(carboxymethyl)-1,4,7,10-tetraazacyclododecan-1-yl)pentanedioic acid), DOTAM (1,4,7,10-tetrakis(carbamoylmethyl)-1,4,7,10-tetraazacyclododecane) and 1,4,8,11-tetraazacyclotetradecane (Cyclam), 1,4,7,10-tetraazacyclododecane (Cyclen), and deferoxamine (DFO).

More particularly, the metal cations M2 are selected from heavy metals, preferably from the group consisting of: Pt, Pd, Sn, Ta, Zr, Tb, Tm, Ce, Dy, Er, Eu, La, Nd, Pr, Lu, Yb, Bi, Hf, Ho, Sm, In and Gd, or a mixture thereof. The metal cations M2 are preferably Bi and/or Gd.

In a particular embodiment, the nanoparticle for the use according to the invention comprises between 3 and 100, preferably between 5 and 20, metal cations M2, in particular of Bi and/or Gd.

The nanoparticle according to the invention enables both the capture of copper and/or iron by the chelating group Ch1, and/or imaging or treatment of tumors by the chelating group Ch2 complexed with a metal cation M2 that has properties of a contrast agent, radiosensitizer or brachytherapy agent.

By way of examples of metal cation M2 that can be used as MRI contrast agent, mention will be made of Gd, Dy, Mn and Fe.

By way of examples of metal cation M2 that can be used as a radiosensitizer, mention will be made of Gd, Lu, Yb and Bi, Hf and Ho, preferably gadolinium or bismuth.

Those skilled in the art will select the n/(n+m) ratio on the basis of the desired effect, and in particular on the basis of the desired treatment, the type of patient, the dose used and/or the patient to be treated. For example, the n/(n+m) ratio is greater than or equal to 20%; in particular between 20% and 100%, preferably between 40% and 60%. In one embodiment, n/(n+m) is equal to 100%. In other words, m, which represents the number of chelating agent Ch2 complexed with a metal cation M2, is equal to 0, and 100% of the chelating groups Ch are complexed with a metal cation M1 or are uncomplexed.

In a more particular embodiment, the chelating group Ch1 is identical to the chelating group Ch2 and corresponds to DOTAGA of the following formula (I) [Chem. 1]

(I)

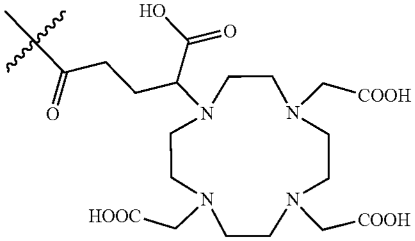

grafted to a matrix PS of the nanoparticle, for example a polysiloxane matrix.

In another more particular embodiment, the chelating group Ch1 is identical to the chelating group Ch2 and corresponds to DOTA of the following formula [Chem. 2]

(II)

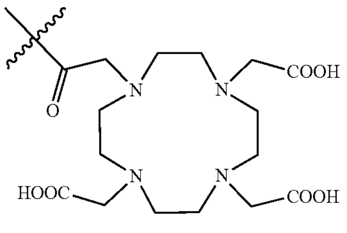

grafted to a matrix PS of the nanoparticle, for example a polysiloxane matrix.

Thus, in one embodiment, the present disclosure relates to a nanoparticle $[Ch1]_n$—PS—$[Ch2]_m$, wherein:

PS is an organic or inorganic polymer matrix,

Ch1 is DOTA or DOTAGA which is uncomplexed or is complexed with a metal cation M1, M1 is absent, or selected from metal cations for which the constant for complex formation with Ch1 is less than that of copper and/or of iron, in particular at least ten times less; for example, M1 is selected from zinc or alkaline-earth metals, in particular calcium or magnesium, Ch2, which is identical to Ch1, is DOTA or DOTAGA and is complexed with a metal cation M2 having a high atomic number Z, greater than 40, and preferably greater than 50, preferably Gd, characterized in that (i) the chelating groups Ch1 and Ch2 are grafted to the polymer matrix, (ii) the n/(n+m) ratio is between 10% and 100%, preferably between 40% and 60%, (iii) the mean hydrodynamic diameter of the nanoparticle is between 1 and 50 nm, preferably between 2 and 20 nm, and more preferentially between 2 and 8 nm.

In a particular, and preferred, embodiment, (n+m), which corresponds to the number of chelating groups Ch1 and Ch2 grafted per nanoparticle (optionally with Ch1 and Ch2 being DOTA or DOTAGA), is between 3 and 100, preferably between 5 and 50, and for example between 10 and 30.

Aside from the chelating function, the nanoparticles according to the present disclosure can be surface-modified (functionalization) by hydrophilic compounds (PEG) and/or loaded differently in order to adapt their biodistribution within the body and/or by targeting molecules to enable specific cell targeting, in particular for targeting specific tissues or tumor cells. The targeting agents are grafted to the polymer matrix and are preferentially present in a proportion of between 1 and 20 targeting agents per nanoparticle and preferably between 1 and 5 targeting agents.

For the surface grafting of the targeting molecules, use may be made of conventional coupling with reactive groups that are present, optionally preceded by an activation step. Coupling reactions are known to those skilled in the art and will be chosen on the basis of the structure of the surface layer of the nanoparticle and on the basis of the functional groups of the targeting molecule. See for example "Bioconjugate Techniques" G. T Hermanson, Academic Press, 1996, in "Fluorescent and Luminescent Probes for Biological Activity", Second Edition, W. T. Mason, ed. Academic Press, 1999. Preferred coupling methods are described below. Preferably, these targeting molecules are grafted to the amine bonds of the nanoparticles, depending on the variant of the nanoparticles, either ultrafine or AGuIX, as described in the next paragraph. The targeting molecules will be chosen on the basis of the envisaged application.

In a specific embodiment, the nanoparticles are functionalized with a targeting agent such as a peptide, an immunoglobulin, a nanobody, a VHH or single domain fragment, an antibody, an aptamer or any other protein that targets, for example, tumor environments, typically an antibody, immunoglobulin or nanobody targeting tumor-associated antigens or certain cancer markers known to those skilled in the art.

Ultrafine Nanoparticles and AGuIX Nanoparticles

In a more particularly preferred embodiment, in particular due to their very small size and their stability, the nanoparticles which may be used are nanoparticles that comprise a polysiloxane matrix PS and that do not comprise a metal oxide-based core, unlike nanoparticles of the core-shell type that comprise a metal oxide-based core and a polysiloxane coating (and that are described in particular in WO2005/088314 and WO2009/053644).

Thus, in a specific embodiment, the nanoparticles according to the present disclosure are nanoparticles based on polysiloxane chelated with gadolinium, of formula $[Ch1]_n$—PS—$[Ch2]_m$, wherein (i) PS is a polysiloxane matrix, (ii) Ch1 and Ch2 are DOTAGA chelating groups of the following formula (I) [Chem. 1]

(I)

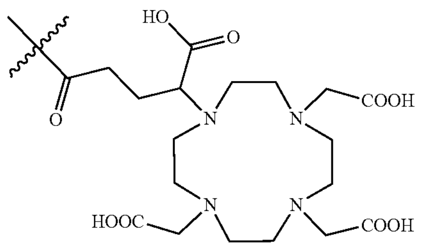

and grafted to the polysiloxane matrix by covalent bonding, (iii) M1 is absent, and M2 is the gadolinium cation $Gd^{3+}$, (iv) n+m is between 5 and 50, preferably between 10 and 30, and (iv) the mean hydrodynamic diameter is between 2 and 8 nm.

More specifically, these nanoparticles based on polysiloxane chelated with gadolinium are ultrafine nanoparticles obtained from AGuIX nanoparticles as starting material.

Such ultrafine AGuIX nanoparticles can be obtained by a top-down synthesis method, described in particular in Mignot et al., Chem Eur J 2013 "A top-down synthesis route to ultrasmall multifunctional Gd-based silica nanoparticles for theranostic applications" DOI: 10.1002/chem.201203003.

Other processes for synthesizing ultrafine nanoparticles are also described in WO2011/135101, WO2018/224684 and WO2019/008040.

The AGuIX nanoparticles which may serve as starting material for obtaining the nanoparticles according to the present disclosure are in particular of the following formula (III) [Chem. 3]

(III)

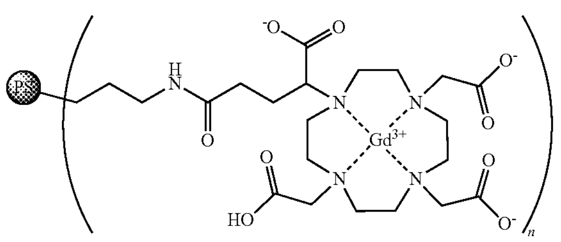

wherein PS is a polysiloxane matrix, and n is on average between 10 and 50, and the nanoparticles have a mean hydrodynamic diameter of 4±2 nm and a weight of approximately 10 kDa.

The AGuX nanoparticles can also be characterized by the following formula (IV) [Chem. 4]

$$(GdSi_{4-7}C_{24-30}N_{5-8}O_{15-25}H_{40-60}, 5\text{-}10\ H_2O)_x \quad (IV)$$

Process for Synthesizing the Nanoparticles According to the Present Disclosure The nanoparticles according to the present disclosure can be obtained by the process for preparing a colloidal solution of nanoparticles comprising chelating groups grafted to a polymer matrix, just a portion of the chelating groups being complexed with a metal cation, the other portion being uncomplexed, said process comprising (1) synthesizing or providing, as starting material, a colloidal solution of nanoparticles NP1 of the following formula $[Ch_2]n$—PS, wherein:

PS is an organic or inorganic polymer matrix,

Ch2 is a chelating group, complexed with a metal cation M2 having a high atomic number Z, greater than 40, and preferably greater than 50, characterized in that (i) Ch2 is grafted to the polymer matrix, (ii) n is between 5 and 100, and (iii) the mean hydrodynamic diameter of the nanoparticle NP1 is between 1 and 50 nm, preferably between 2 and 20 nm, and more preferentially between 2 and 8 nm (2) a step of treating the colloidal solution of nanoparticles NP1 in an acid medium, for example by adding a solution of hydrochloric acid, in order to obtain a pH of less than 2.0, preferably less than 1.0, for a sufficient duration to obtain partial or complete salting-out of the metal cations M2, (3) where appropriate, a step of diluting the solution, for example with water, (4) a step of purification to separate the nanoparticles obtained in step (2) from the free metal cations M2, (5) where appropriate, a step of concentrating the solution of nanoparticles obtained in step (4), (6) where appropriate, repeating steps (3), (4) and (5), (7) where appropriate, freezing and/or lyophilizing the solution of nanoparticles obtained in one of steps (4), (5) or (6).

Such a process makes it possible to obtain nanoparticles $[Ch1]n—PS—[Ch2]_m$ in which Ch1 and Ch2 are identical. The process thus advantageously makes it possible to obtain partial or complete salting-out of the metal cations M2 that were initially complexed with the chelating group Ch2 on the nanoparticle NP1. Those skilled in the art will be able to modulate the degree of salting-out of the metal cations M2 and therefore the mean n/(n+m) ratio in the final solution, in particular by adjusting the pH and the duration of the treatment step (2).

In a preferred embodiment, the nanoparticles NP1 are ultrafine or AGuIX nanoparticles as defined in the previous section and are complexed with the gadolinium cation. Specific embodiments are given in the examples. Typically, the duration of the treatment in step (2) can be between 0.5 and 8 hours, for example between 2 and 6 hours at a pH of less than 1.0.

The nanoparticles obtained according to the above process can, where appropriate, then be functionalized by other chelating groups, different from Ch2 and/or targeting agents or hydrophilic molecules.

In one embodiment, the nanoparticles obtained according to the above process are brought into contact with metal cation M1 in order to achieve complexation of at least a portion of the free chelating groups with the metal cation M1, so as to obtain nanoparticle of the following formula:

$$[Ch1]_n—PS—[Ch2]_m,$$

wherein:

PS is an organic or inorganic polymer matrix,

Ch1 is a chelating group which is partially complexed with a metal cation M1,

M1 is selected from metal cations for which the constant for complex formation with Ch1 is less than that of copper and/or of iron, in particular at least ten times less; for example, M1 is selected from zinc, calcium, magnesium or other alkaline-earth metals, Ch2 is a chelating group, identical to Ch1, and complexed with a metal cation M2 having a high atomic number Z, greater than 40, and preferably greater than 50, characterized in that (i) the chelating groups Ch1 and Ch2 are grafted to the polymer matrix, (ii) the n/(n+m) ratio is between 10% and 100%, preferably between 40% and 60%, and (iii) the mean hydrodynamic diameter of the nanoparticle is between 1 and 50 nm, preferably between 2 and 20 nm, and more preferentially between 2 and 8 nm.

Pharmaceutical Formulations of the Nanoparticles According to the Present Disclosure The compositions comprising the nanoparticles according to the present disclosure are administered in the form of colloidal suspensions of nanoparticles.

They can be prepared as described here or according to other methods known to those skilled in the art, and be administered by different local or systemic routes depending on the treatment and the region to be treated.

Thus, the present disclosure relates to a colloidal suspension of nanoparticles of formula $[Ch1]_n—PS—[Ch2]_m$ as described in the preceding sections, and the pharmaceutical compositions comprising these colloidal suspensions, where appropriate, in combination with one or more pharmaceutically acceptable excipients.

The pharmaceutical compositions may in particular be formulated in the form of lyophilized powders or aqueous solutions for intravenous injection. In a preferred embodiment, the pharmaceutical composition comprises a colloidal solution with a therapeutically effective amount of nanoparticles of formula $[Ch1]_n—PS—[Ch2]_m$ as described in the preceding sections, in particular nanoparticles based on polysiloxane chelated with gadolinium, and more specifically as obtained from AGuIX nanoparticles, as described above.

In some embodiments, it is a lyophilized powder comprising between 200 mg and 15 g, preferably between 250 and 1250 mg of nanoparticles, per vial. The powder may further comprise other excipients, and in particular $CaCl_2$.

The lyophilized powders can be reconstituted in an aqueous solution, typically sterile water for injection. Thus, the present disclosure relates to a pharmaceutical composition for the use thereof as a solution for injection, comprising, as active ingredient, the nanoparticles of formula $[Ch1]_n—PS—[Ch2]_m$ as described in the preceding sections, in particular nanoparticles based on polysiloxane chelated with gadolinium, and more specifically as obtained from AGuIX nanoparticles, as described above.

In one embodiment, the pharmaceutical composition is characterized in that it is an injectable composition for intravenous or intratumoral administration, or an aerosol for intrapulmonary administration, in particular comprising an effective amount of chelating group Ch1 for the in vivo capture of copper and/or of iron in the tumor, the chelator Ch1 being for example at a concentration of at least 10 mM in the composition.

For example, for the uses thereof as described below, in particular for the treatment of a tumor by the in vivo capture of copper and/or iron, the composition is an injectable solution comprising nanoparticles based on polysiloxane chelated with gadolinium at a concentration of between 50 and 200 mg/ml, for example between 80 and 120 mg/ml.

Uses of the Nanoparticles

Due to the presence of chelating groups Ch1 that are free or complexed with metal cations M1, the nanoparticles according to the present invention enable the capture of endogenous copper and/or iron after they are administered to a subject in need thereof. Endogenous copper capture preferably means the local capture of an amount of between 100 ppb (0.1 mg of copper per liter) and 10 000 ppb (10 mg of copper per liter) of endogenous copper. Thus, the present disclosure more particularly targets a process for capturing endogenous copper in a subject, in particular a subject suffering from cancer.

Endogenous iron capture preferably means the local capture of an amount of between 100 ppb (0.1 mg of iron per liter) and 10 000 ppb (10 mg of iron per liter) of endogenous iron. Thus, the present disclosure more particularly targets a process for capturing endogenous iron in a subject, in particular a subject suffering from cancer.

If the nanoparticles are administered intravenously or pulmonarily, the copper and/or iron can be captured within the general blood circulation then, later, within the tumors, after the nanoparticles have accumulated in the tumors, particularly by passive targeting associated with the EPR effect. This effect of passive targeting of tumors and accumulation has been clearly demonstrated in particular by ultrafine nanoparticles of AGuIX type.

The disclosure therefore also relates to a process for treating tumors in a subject, said process comprising administering, to said subject, an effective amount of a pharmaceutical composition of nanoparticles of formula $[Ch1]_n$—PS—$[Ch2]_m$ as described in the ceding sections, in particular nanoparticles based on polysiloxane chelated with gadolinium, and more specifically as obtained from AGuIX nanoparticles, as described above, and characterized in that the nanoparticles enable the treatment of the tumor, in part by capturing endogenous copper and/or iron.

In a particular embodiment of said process, the composition also comprises an effective amount of metal cation M2, preferably gadolinium or bismuth, for use as a radiosensitizer, and the process comprises, after administering the composition, a step of irradiating the subject with an effective dose for the treatment of the tumor by radiotherapy.

“Patient” or “subject” preferably means a mammal or a human, including for example a subject who has a tumor.

The terms “treatment” and “therapy” relate to any act, the aim of which is to improve the health of a patient, such as therapy, and delaying the progression of a disease. In some cases, these terms relate to the improvement or eradication of a disease or of symptoms associated with the disease. In other embodiments, these terms relate to a reduction in the spread or worsening of the disease, resulting from the administration of one or more therapeutic agents to a subject suffering from such a disease. In the context of the treatment of tumors, the term “treatment” can typically encompass a treatment that enables the growth of a tumor to be stopped, the size of the tumor to be reduced, and/or the tumor to be eliminated.

In particular, the nanoparticles are used for the treatment of solid tumors, for example brain cancer (primary and secondary, glioblastoma, etc.), liver cancers (primary and secondary), cancers of the pelvic region (cervical cancer, prostate cancer, anorectal cancer, colorectal cancer), cancers of the upper aerodigestive tract, lung cancers, esophageal cancer, breast cancer, pancreatic cancer.

“Effective amount” of nanoparticles refers to the amount of nanoparticles as described above which, when administered to a patient, is sufficient to be located in the tumor and to enable treatment of the tumor by capturing endogenous copper and/or iron, where appropriate in combination with a radiosensitizing effect and radiotherapy treatment.

This amount is determined and adjusted based on factors such as the age, sex and weight of the subject.

The nanoparticles as described above may be administered intratumorally, subcutaneously, intramuscularly, intravenously, intradermally, intraperitoneally, orally, sublingually, rectally, vaginally, intranasally, by inhalation or by transdermal application. They are preferably administered intratumorally and/or intravenously.

Irradiation methods for the treatment of tumors after administration of nanoparticles as radiosensitizer are well known to those skilled in the art and have been described in particular in the following publications: WO2018/224684, WO2019/008040 and C. Verry et al., Science Advances, 2020, 6, eaay5279 ; and C. Verry et al., “NANO-RAD, a phase I study protocol”, BMJ Open, 2019, 9, e023591.

The total irradiation dose during radiotherapy will be adjusted depending on the type of cancer, the stage and the subject to be treated. For a curative dose, a typical total dose for a solid tumor is approximately 20 to 120 Gy. Other factors may be taken into account, such as treatment by chemotherapy, comorbidity, and/or the fact that the radiotherapy takes place before or after a surgical intervention. The total dose is generally split into fractions. The radiotherapy step in the process according to the present disclosure may for example comprise several fractions of between 2 and 6 Gy per day, for example 5 days a week, and in particular over 2 to 8 consecutive weeks, it being possible for the total dose to be between 20 and 40 Gy, for example 30 Gy.

The nanoparticles according to the present disclosure may be administered alone or in combination with one or more other active ingredients, and in particular other medicaments such as cytotoxic or anti-proliferative agents or other anticancer agents and in particular immune checkpoint inhibitors. Combined administration means simultaneous or sequential (at different times) administration.

EXAMPLES

Materials and Methods

The CuPRiX$_x$ products are obtained by introducing the starting product AGuIX®, provided by Nh TherAguix (France), into a highly acid medium obtained from 37% extra-pure hydrochloric acid originating from CarlRoth.

The filtration steps are carried out using a peristaltic pump and a Vivaflow 200®-5kDa cassette from Sartorius Stedim Biotech (France), used following the conditions described in the manual for Vivaflow 200®.

The measurement of the hydrodynamic diameter, and the titration of the isoelectric point, are carried out using a Zetasizer Nano-S (633 nm He-Ne laser) from Malvern Instruments (USA). For the measurement of the isoelectric point, this apparatus is coupled with an MPT-2 automatic titrator from Malvern Instruments (USA).

HPLC-UV is carried out using an Agilent 1200 with a DAD detector. The reverse phase column used is a C4, 5 µm, 300 Å, 150×4.6 mm from Jupiter. Detection is performed by a UV detector at a wavelength of 295 nm. The gradient of the phases A ($H_20$/ACN/TFA: 98.9/1/0.1) and B ($H_20$/ACN/TFA: 10/89.9/0.1) is as follows: 5 minutes at 95/5 followed by a linear gradient over 10 min, making it possible to reach the ratio 10/90 which is maintained for 15 minutes. At the end of these 15 minutes, the content of A is brought back to 95% in 1 minute and is followed by a 7-minute plateau at 95/5. The products used in the composition of the eluent phases are all certified HPLC-grade.

Elemental analysis was carried out at the Institut des Sciences Analytiques, UMR 5280, Pole Isotopes & Organique, 5 rue de la Doua, 69100 Villeurbanne.

HPLC-ICP/MS is carried out using Nexion 2000 from Perkin-Elmer (USA). The free elements in the medium are measured in isocratic mode using an elution phase having the following composition: 95% A and 5% B. The composition of phases A and B is identical to the HPL-UV method. The reverse phase column used is a C4, 5 µm, 300 Å, 150×4.6 mm from Jupiter. The products used in the composition of the eluant phases are all certified HPLC-grade.

The particles are lyophilized via an Alpha 2-4 LSC lyophilizer from Christ (Germany), following the "primary desiccation" program.

The A549 cells (ECACC 86012804) are cultured in F12-K medium (Gibco™, Thermofischer) supplemented with 10% fetal calf serum (Dutscher) and 1% penicillin-streptomycin (Gibco™, Thermofischer). For each experiment, the cells are rinsed twice in PBS 1× (Gibco™, Thermofischer), incubated for 5 minutes in an incubator at 37° C., 5% $CO_2$ with trypsin-EDTA, then taken up in complete medium.

At least 1 h before the test, the products $CuPRiX_{20}$ and $CuPRiX_{30}$ are taken up in sterile distilled water at a free DOTA concentration equal to 10 mM (respectively 30 mM and 16.7 mM of gadolinium) and stored at 4° C.

For the migration and invasion test, the A549 cells are seeded (50 000 cells/well) in ImageLock 96-well plates (Essen BioScience) and incubated for 16 h at 37° C. and 5% $CO_2$ until 90-100% confluence is reached. The WoundMaker™ (Essen BioScience) is used to create wounds in the cell monolayer of each well. Each well is then rinsed twice with PBS 1×. For invasion, 50 µl of Matrigel (Corning)—diluted beforehand in F12-K medium containing or not containing $CuPRiX_{20}$ —at a final concentration of 1 mg/ml, are added to each well. The plate is incubated for 30 minutes at 37° C., to enable polymerization of the Matrigel. Finally, 100 µl of medium containing increasing concentrations of CuPRiX are added to each well (containing or not containing Matrigel). The plate is placed in the Incucyte (10× objective) and images of the filling of the wounds are taken automatically every 2 h by the Zoom Incucyte software (Essen BioScience) in the incubator containing CO2. The data is analyzed by the software and the results are expressed as the percentage confluence of the wounds.

For the chemotactic migration test, the A549 cells are trypsinized, centrifuged then resuspended in depleted medium (FCS-free F12-K). The cells are subsequently seeded (1000 cells per well, 40 µl per well) in the IncuCyte® Clearview insert (Essen BioScience). In the corresponding wells, 20 µl of depleted medium, containing or not containing $CuPRiX_{20}$ (500 µM of free chelate) are added. Finally, 200 µl of F-12K medium containing 10% FCS and containing or not containing $CuPRiX_{20}$ (500 µM of free chelate) are added to the lower compartment of the chemotaxis chamber. Images of each insert are taken every hour. The chemotactic migration from the upper reservoir to the lower reservoir is quantified as the cell confluence below the membrane compared to the initial confluence of cells seeded above the membrane. The calculation is performed automatically using the IncuCyte ZOOM 2015A microscopy software.

For the test of migration after irradiation, the A549 cells are cultured in ImageLock® 96-well culture plates (Essen BioScience) at 20 000 cells per well, overnight at 37° C., 5% $CO_2$. The cells are treated with FCS-free F-12K, containing or not containing $CuPRiX_{30}$ (500 µM of free chelate, equivalent to 800 µM of gadolinium) for 24 h then they are irradiated at 8 Gy (X-Rad320 irradiator, 250 kV, 15 mA). After irradiation, the wound is made using the 96-well WoundMaker™ (Essen BioScience). The cells are rinsed twice with PBS 1× to remove floating cells and 100 µl of medium containing $CuPRiX_{30}$ (0 and 500 µM of free chelate, equivalent to approximately 0 and 800 µM of gadolinium) are added to each corresponding well.

To evaluate clonogenic survival, the cells are seeded at 40 000 cells/$cm^2$, i.e. 1 million cells in a 25$cm^2$ flask (Dutscher) and incubated overnight at 37° C., 5% $CO_2$. The cells are treated with FCS-free medium, containing or not containing $CuPRiX_{30}$ (500 µM of free chelate, equivalent to 800 µM of gadolinium) for 24 h. The cells were then irradiated at different doses (0, 2, 3, 4, 6 and 8 Gy). After irradiation, the cells are washed in PBS 1×, trypsinized and counted. The cells are then reseeded in 25 $cm^2$ flasks and grow over six divisions (7 days) before being fixed and stained. The colonies are fixed using a 96% ethanol solution (VWR) for 30 minutes, then stained with a Giemsa solution (Sigma-Aldrich) diluted to 1/20 for 30 minutes. The flasks are subsequently rinsed, then the colonies containing 64 cells or more were counted digitally using the Colcount™ colony counter (Oxford Optronix). Clonogenic survival was determined using a linear quadratic model of the form $SF=e^{-(\alpha D+\beta D^2)}$, where SF is the surviving fraction, and α and β represent the probabilities of lethal and sublethal damage, respectively.

The line 4T1 is a breast cancer cell line derived from the mammary gland of a BALB/c mouse strain. The cells are cultured in RPMI medium (Gibco™, Thermofischer) supplemented with 10% FCS and 1% penicillin-streptomycin.

The upper aerodigestive tract (UAT) cancer cell line SQ20B is derived from a recurrent laryngeal cancer. The sub-population of interest, SQ20B/CSCs (Stem-cell like cancer cells), was collected after two consecutive steps of cell sorting (Hoechst efflux and CD44 labeling) carried out using flow cytometry. This population has low expression of EGFR and a mesenchymal phenotype, associated with the acquisition of migratory and invasive properties. These cells, SQ20B-CSCs, are cultured in DMEM:F12 medium (3:1, v:v) supplemented with 5% FCS, 1% PS, 0.04 mg/ml hydrocortisone and 20 ng/ml of epidermal growth factor (EGF).

The in vivo study protocol (2021021714569264) was accepted by the ethics committee of the Université Claude Bernard Lyon 1. The study was carried out on a triple-negative breast cancer mouse model (cell line 4T1). 7-Week-old female BALB/c mice (Janvier Labs) were used. The 4T1 cells (5 x $10^5$, matrigel 50:50) were injected subcutaneously into the $4^{th}$ mammary pad under isoflurane anesthesia. This location was chosen in order to spare vital tissues during the radiotherapy treatment. Ten days after transplant, the mice were randomly split into 2 groups: the NaCl (control) group (n=4) and the CuPRiX group (n=6). The mice received 3 injections of 50 μl each intravenously, spaced apart by 48 h, of NaCl 0.9% (control) or CuPRiX (200 mg/kg). The mice were weighed, their general condition was evaluated and the tumors were measured 3 times a week. The mice were euthanized 5 days after the final injection, and the metastases were quantified in the target organs (lungs and liver).

The metastases were quantified according to the protocol of Pulaski et al (2000). To this end, after the mice were euthanized by cervical dislocation under isoflurane anesthesia, the lungs and liver were removed. The organs are washed with HBSS, cut up mechanically then subjected to enzymatic digestion by type IV collagenase (2 mg/ml) associated with DNAse I (Roche) for the lungs and a type I collagenase (2 mg/ml), BSA (1 mg/ml) and hyaluronidase (2 mg/ml) cocktail for the livers. This digestion takes place for 2 hours (lungs) and 40 minutes (livers) at 37° C. on a rotating wheel. The digested organs are subsequently filtered through 70 pm nylon filters. They are centrifuged at 1500 G for 5 minutes and washed twice with HBSS. The cell pellets are resuspended in RPMI medium containing 60 μM of 6-thioguanine for the study of clonogenic growth. The suspensions are placed back in culture, diluted to 1/6 for the lungs and pure for the livers, in 10 cm petri dishes. After 8 days, the cells are fixed with 96% ethanol and stained with Giemsa (diluted to 1/20 in distilled water). The clones are subsequently counted digitally using the Colcount™ colony counter (Oxford Optronix).

Example 1: Acidification of the Medium and Salting-Out of $Gd^{3+}$ Ions

In order to obtain a nanoparticle capable of complexing copper ions while retaining its properties as a radiosensitizer, the product AGuIX® was placed in acid medium with the aim of protonating the DOTA groups and thus releasing a portion of the initially-complexed $Gd^{3+}$ ions.

Firstly, a 200 g/l solution of AGuIX® was prepared by dissolving 10 g of product in 50 ml of UltraPure water. The solution was left under stirring at ambient temperature for 1 h. In parallel, a 2 M hydrochloric acid solution was prepared by adding 10 ml of 37% hydrochloric acid (37% hydrochloric acid, extrapure, 2.5 I, plastic, CarlRoth) to 50 ml of UltraPure water.

After one hour of stirring, 50 ml of the 2 M hydrochloric acid solution are added to the 50 ml of AGuIX®. The pH was then measured and is less than 0.5. The solution obtained is orangey brown in color. The set-up is left in an oven preheated to 50° C. for 4 hours. A sample was taken off every hour in order to observe, by HPLC-ICP/MS, the salting-out of the gadolinium ions (FIG. 1). It is observed that the peak of free $Gd^{3+}$ in the medium at the retention time Tr=2.3 min increases with the reaction time.

Example 2: $CuPRiX_{20}$: 4 h of Reaction

After 4 h, the solution was diluted 10-fold with UltraPure water. The pH is then measured and brought to 1±0.2, if necessary, with 1 M sodium hydroxide so as not to destroy the filtration membrane. The 500 ml of solution thus obtained were purified by means of a peristaltic pump and a Sartorius Vivaflow 200-5 kDa cassette in order to separate the particles from the released $Gd^{3+}$ in order to prevent these ions from re-complexing.

The initial volume of 500 ml is concentrated to 50 ml and the operation is repeated. In total, the dilution/concentration operation was repeated 4 times and the final volume is 50 ml. Following purification, the 50 ml of solution were distributed in vials, each containing 2 ml of solution. The vials are placed at −80° C. in order to freeze the solution, then lyophilized to obtain our final product in the form of a brown-colored powder.

Once the product is obtained, a vial is taken from the batch in order to characterize the product. A 1 ml solution at 100 g/l of the new product is prepared by adding UltraPure water. After 1 hour in solution, the diameter was measured using our DLS apparatus, indicating a diameter of 4.4 nm±1.2 nm. The HPLC-UV/Vis chromatogram was carried out, and indicates a retention time of 11 min±0.1 min, identical to the original particles. The isoelectric point of $CuPRiX_{20}$ was also measured and is equal to 6.29, superior to the isoelectric point of AGuIX® which is equal to 7.15. Since gadolinium has magnetic properties, the relaxivity constant ri of $CuPRiX_{20}$ was measured, and is equal to 18.9 $mM^{-1} \cdot s^{-1}$ per atom of gadolinium.

Example 3: Assay of the Number of Free DOTAGA by Europium Chelation and Fluorescence The amount of free chelates present in the $CuPRiX_{20}$ can be determined by chelation of europium followed by study of the luminescence. This is because europium has luminescence mainly centered around 590 (5D0->7F1) et 615 nm (5D0 ->7F2). This luminescence is quenched in the presence of water molecules. The principle of the assay is to add increasing amounts of europium: as it is chelated, the luminescence increases, then when all the chelation sites are full, the luminescence reaches a plateau, as shown in FIG. 2.

In order to carry out the assay, $CuPRiX_{20}$ was placed in an acetate buffer at pH 5; a europium chloride salt dissolved in the acetate buffer is added. An assay curve is then plotted, performing excitation at 396 nm and reading off emission at 590 nm. This assay makes it possible to calculate an amount of chelate of 0.16 pmol per mg of $CuPRiX_{20}$. Given that there is a zero, or at most negligible, amount of gadolinium in the initial AGuIX® product, then the initial amount of gadolinium is equal to the amount of DOTA. The initial gadolinium content in the starting product, measured by elemental analysis, was 0.81 μmol per mg of AGuIX®.

The product $CuPRiX_{20}$ thus has 20% of its DOTA groups free.

Example 4: Copper Chelation

The presence of free DOTA thus indicates a potential application of $CuPRiX_{20}$ as a possible chelator in the context of chelation therapy. The complex-forming potential of $CuPRiX_{20}$ was determined by chelation of copper followed by a study of the absorbance using HPLC-UV/Vis. The DOTA@Cu has an absorbance at 295 nm that is far greater than those of the DOTA@Gd complex, DOTA and copper ions in solution.

The absorbance of $CuPRiX_{20}$ will increase as the free DOTA groups complex the available copper ions, until it reaches a plateau at which the addition of additional copper will not lead to an increase in absorbance. To carry out this experiment, a series of samples was thus prepared with an increasing amount of copper chloride solution and a constant amount of $CuPRiX_{20}$. The volumes of all the samples are equalized. This experiment makes it possible to calculate an amount of complexable copper of 0.18 μmol per mg of $CuPRiX_{20}$. An identical experiment carried out on the starting product AGuIX® indicates the large increase in the chelating potential of $CuPRiX_{20}$ (FIG. 3).

Example 5: $CuPRiX_{30}$: 5 h of Reaction

The content of free DOTA can be modified on the basis of the reaction time of AGuIX in acid medium. After 5 h, the solution was diluted 10-fold with UltraPure water. The pH is then measured and brought to 1±0.2, if necessary, with 1 M sodium hydroxide so as not to destroy the filtration membrane. The 500 ml of solution thus obtained were purified by means of a peristaltic pump and a Sartorius Vivaflow 200 -5 kDa cassette in order to separate the particles from the released $Gd^{3+}$ in order to prevent these ions from re-complexing. The initial volume of 500 ml is concentrated to 50 and the operation is repeated.

In total, the dilution/concentration operation was repeated 4 times and the final volume is 50 ml. Following purification, the 50 ml of solution are distributed in vials, each containing 2 ml of solution. The vials are placed at −80° C. in order to freeze the solution, then lyophilized to obtain our final product $CuPRiX_{30}$ in the form of a brown-colored powder. Once the product is obtained, a vial was taken from the batch in order to characterize the product.

A 1 ml solution at 100 g/l of the new product was prepared by adding UltraPure water. After 1 hour in solution, the diameter was measured using our DLS apparatus, indicating a diameter of 5.7 nm±1 nm. The HPLC-UV/Vis chromatogram was carried out, and indicates a retention time of 10.8 min±0.1 min, identical to the original particles.

Example 6: $CuPRiX_{30}$: Improving the Complex-Forming Potential Compared to $CuPRiX_{20}$ The presence of free DOTA thus indicates a potential application of $CuPRiX_{30}$ as a possible chelator in the context of chelation therapy. The complexation potential of $CuPRiX_{20}$ was determined by chelation of copper followed by a study of the absorbance using HPLC-UV/Vis. The DOTA@Cu has an absorbance at 295 nm that is far greater than those of the DOTA@Gd complex, DOTA and copper ions in solution. The absorbance of the product will increase as the free DOTA groups complex the available copper ions, until it reaches a plateau at which the addition of additional copper will not lead to an increase in absorbance.

To carry out this experiment, a series of samples was thus prepared with an increasing amount of copper chloride solution and a constant amount of $CuPRiX_{20}$. The volumes of all the samples are equalized. This experiment makes it possible to calculate an amount of complexable copper of 0.24 μmol per mg of $CuPRiX_{30}$. The product $CuPRiX_{30}$ thus has 30% of its DOTA groups free.

Example 7: Analysis of the Effect of CuPRiX20 on the Motility of A549 Cells

Cell migration is a multiple-step process that is a fundamental component of many biological processes and disease processes, including in tumor metastasis. In vitro, a wound test is based on the formation of a wound on a cell lawn and the study of cell motility, i.e. the ability of the cells to move over a surface in response to a change in density, closing the wound in the process. It is a direct measure of the motility of the cells over a solid 2D substrate.

The aim of this example was to show the capacity of $CuPRiX_{20}$ to reduce cell motility. The A549 cells were cultured in F12-K medium (Gibco) containing 8 nM of CuSO4-5H2O. After being cultured for 72 h, with or without $CuPRiX_{20}$ (500 μM of free chelate), the cells were trypsinized then seeded at 40 000 cells per well in an ImageLock® 96-well culture plate (Essen BioScience). The plate was placed overnight at 37° C., 5% $CO_2$. The wound was then made using the IncuCyte® WoundMaker (Essen BioScience). The cells were rinsed twice with PBS to remove floating cells, then treated with 100 μl of medium containing increasing concentrations of $CuPRiX_{20}$ (0, 50, 100, 200, 300, 400, 500 and 1000 μM of free chelate, equivalent to approximately 0, 150, 300, 600, 900, 1200, 1500 and 3000 μM of gadolinium).

Images of the filling of the wounds were taken automatically every 2 h for 72 h by the Zoom Incucyte software (Essen BioScience) in the incubator containing $CO_2$. The data was analyzed by the software and the results are expressed as the percentage confluence of the wound. The results obtained made it possible to demonstrate slowing of cell motility of the A549 cells, due to treatment with CuPRiX20 at different concentrations (FIG. 4, FIG. 5 and FIG. 6).

Example 8: Comparison of the Effect of CuPRiX20 and CuPRiX30 on the Motility of A549 Cells The aim of this example is to show the capacity of CuPRiX20 and CuPRiX30 to reduce cell motility, and to compare their effects. The A549 cells were cultured in ImageLock® 96-well culture plates (Essen BioScience) at 40 000 cells per well, overnight at 37° C., 5% CO2. The wound test was carried out using the 96-well IncuCyte® WoundMaker (Essen BioScience). The cells were rinsed twice with PBS to remove floating cells and were then treated with 100 μl of medium containing CuPRiX20 (0, 125, 250 and 500 μM of free chelate, equivalent to approximately 0, 375, 750 and 1500 μM of gadolinium) or CuPRiX30 (0, 125, 250 and 500 μM of free chelate, equivalent to approximately 0, 200, 400 and 800 μM of gadolinium.

Images of the filling of the wounds were taken automatically every 2 h by the Zoom Incucyte software (Essen BioScience) in the incubator containing CO2. The data was analyzed by the software and the results are expressed as the percentage confluence of the wounds.

The results obtained made it possible to show that, at a constant concentration of free chelate, the effect of the two types of CuPRiX is equivalent.

Example 9: Analysis of the Effect of CuPRiX20 on the Invasion of A549 Cells

Cellular invasion is one of the characteristics of cancer. It is linked to cell migration and plays a pivotal role in the development of metastases. The ability of tumor cells to form metastases is chiefly determined by the ability of the cell to change and reorganize its cellular morphology and to degrade the extracellular matrix (ECM). In vitro, invasion tests are based on the wound test approach, but include the addition of a gel matrix that mimics the ECM. The addition of the 3D matrix means that the cells have to degrade this matrix in order to move.

The aim of this example is to show the capacity of $CuPRiX_{20}$ to reduce cellular invasion, i.e. the ability of the cells to decompose an extracellular matrix and to move. The A549 cells were cultured in ImageLock® 96-well culture plates at 40 000 cells per well, overnight at 37° C., 5% $CO_2$.

The wound was then made using the IncuCyte® Wound-Maker (Essen BioScience), then the cells were rinsed twice with PBS. 50 μl of Matrigel (Corning)—diluted beforehand in F12-K medium containing or not containing $CuPRiX_{20}$—at a final concentration of 1 mg/ml, were added to each well. The plate was incubated for 30 minutes at 37° C., to enable polymerization of the Matrigel. Finally, 100 μl of medium containing or not containing $CuPRiX_{20}$ (0 and 500 μM of free chelate were added. Images of the filling of the wounds were taken automatically every 2 h for 72 h by the Zoom Incucyte software Essen BioScience) in the incubator containing $CO_2$. The data was analyzed by the Zoom Incucyte software (Essen BioScience) and the results are expressed as the percentage confluence of the wound. The results obtained made it possible to demonstrate slowing of the cellular invasion of the A549 cells, due to treatment with $CuPRiX_{20}$ (FIG. 7).

Example 10: Effect of CuPRiX20 on the Chemotactic Migration of A549 Cells

Chemotactic migration is the directional movement of cells in response to a stimulus. This test consists of a culture insert placed within a well of a cell culture plate. The cells are seeded into the insert, which contains a membrane with a defined pore size, with serum-free medium in order to starve them. The chemoattractant medium is placed in the well underneath. Due to this chemical gradient, cells that are able to migrate are attracted by the chemoattractant medium and pass through the pores. The aim of this example is to show the capacity of CuPRiX20 to reduce cell mobility using a chemotaxis assay. To this end, the IncuCyte ZOOM chemotaxis module was used. The A549 cells (1000 cells/well) were resuspended in F-12K medium containing 0% FCS and were seeded in the upper compartment of a 96-well Cell Migration Incucyte ClearView plate with 8 μm pores (40 μl/well). In the appropriate wells, 20 μl of FCS-free F12-K medium, containing or not containing CuPRiX20 (500 μM of final free chelate) were added. Finally, 200 μl of F-12K medium containing 10% FCS and containing or not containing CuPRiX20 (500 μM of free chelate) were added to the lower compartment of the chemotaxis chamber. Images of each insert were taken every hour. The chemotactic migration from the upper reservoir to the lower reservoir was quantified as the cell confluence below the membrane compared to the initial confluence of cells seeded above the membrane. The calculation was performed automatically using the IncuCyte ZOOM 2015A microscopy software.

The results obtained made it possible to demonstrate a large reduction in the chemotactic migration of the cells by CuPRiX20 (FIG. 8).

Example 11: Effect of the Combination of CuPRiX30 and Photon Irradiation on the Motility of A549 Cells The aim of this example is to show the capacity of CuPRiX30 to reduce cell mobility after photon irradiation. The A549 cells were cultured in ImageLock® 96-well culture plates at 20 000 cells per well, overnight at 37° C., 5% $CO_2$. The cells were incubated with FCS-free F-12K, containing or not containing CuPRiX30 (500 μM of free chelate, equivalent to 800 μM of gadolinium) for 24 h. The cells were subsequently irradiated at 8 Gy (X-Rad320 irradiator, 250 kV), then the wound was made. The cells were rinsed twice with PBS to remove floating cells and 100 μl of medium containing CuPRiX30 (0 and 500 μM of free chelate, equivalent to approximately 0 and 800 μM of gadolinium) were added to each corresponding well.

Images of the filling of the wounds were taken automatically every 2 h by the Zoom Incucyte software in the incubator containing $CO_2$. The data was analyzed by the software and the results are expressed as the percentage confluence of the wounds. The results obtained made it possible to show a superior efficacy (additive effect) of the CuPRiX30/irradiation combination in limiting motility compared to treatment by irradiation alone or by CuPRiX30 alone (FIG. 9).

Example 12: Effect of the Combination of CuPRiX30 and Photon Irradiation on the Survival of A549 Cells A549 cells were seeded at 40 000 cells/cm2, i.e. 1 million cells in a T25cm2 flask, and incubated overnight at 37° C., 5% CO2. The cells were treated with FCS-free F-12K medium, containing or not containing CuPRiX30 (500 μM of free chelate, equivalent to 800 μM of gadolinium) for 24 h. The cells were then irradiated at different doses (0, 2, 3, 4, 6 and 8 Gy). After irradiation, the cells were washed in PBS, trypsinized and counted. The cells were then reseeded in 25 cm2 flasks and were able to grow over six divisions (7 days) before being fixed and stained. Colonies containing 64 cells or more were counted digitally. Clonogenic survival was determined using a linear quadratic model of the form $SF=e^{-(\alpha D+\beta D_2)}$, where SF is the surviving fraction, and α and β represent the probabilities of lethal and sublethal damage, respectively. The results obtained show a reduction in cell survival after irradiation in the presence of $CuPRiX_{30}$ (FIG. 10).

Example 13: Effect of the Combination of $CuPRiX_{30}$ and Photon Irradiation on the Survival of A549, SQ20B-CD44$^+$ and 4T1 Cells For each cell line, the cells were seeded at 40 000 cells/cm2, i.e. 1 million cells in a 25 cm2 flask, and incubated overnight at 37° C., 5% $CO_2$. The medium is then removed and replaced with FCS-free medium alone, containing CuPRiX3o (500 μM of free chelate, equivalent to 800 μM of gadolinium) or AGuIX® (800 μM of gadolinium) for 24 h. The cells are then irradiated at different doses (0, 2, 3, 4, and 6 Gy). After irradiation, the cells are washed in PBS, trypsinized and counted. They are then reseeded in 25 cm2 flasks and are able to grow over six divisions (7 days) before being fixed with 96% ethanol and stained with Giemsa. Colonies containing 64 cells or more are counted digitally. Clonogenic survival was determined using a linear quadratic model of the form $SF=e^{-(\alpha D+\beta D_2)}$, where SF is the surviving fraction, and α and β represent the probabilities of lethal and sublethal damage, respectively. For the 3 cell lines, the results obtained show a reduction in cell survival after irradiation and after treatment with AGuIX and $CuPRiX_{30}$. In the case of the A549 and SQ20B-CD44+ lines, the efficacy of $CuPRiX_{30}$ appears to be equal to that of AGuIX, while it is superior to AGuIX in the case of the 4T1 line (FIG. 11).

Example 14: Efficacy of $CuPRiX_{30}$ on Tumor Growth and the Formation of Metastases in a Metastatic Breast Cancer Mouse Model The aim of this example is to show the capacity of $CuPRiX_{30}$ to slow tumor growth and reduce the formation of metastases. To this end, ten 8-week-old female BALB/c mice were given a subcutaneous injection of 50 000 4T1 cells (triple-negative breast cancer cells, 50:50 PBS:Matrigel). Ten days later (D10), when the tumors had reached 100 $mm^3$ on average, the mice were given an intravenous injection of 50 μl of $CuPRiX_{30}$ (200 mg/kg, n=6) or NaCl (0.9%, n=4). Two more injections were administered 48 h (D12) and 96 h (D14) after the first. Nineteen days after the tumor inoculation, i.e. 5 days after the last injection, the mice were euthanized by cervical dislocation under isoflurane anesthesia, and the organs that might have metastases (lungs and liver) were removed.

To quantify the metastases, the lungs and liver were broken down mechanically then subjected to enzymatic digestion before being filtered. The cell suspensions were subsequently cultured pure (livers) or diluted (lungs) in culture medium containing 60 μM of 6-thioguanine (selective agent for 4T1 cells), and incubated at 37° C. in an incubator containing $CO_2$. Eight days later, the cells are fixed and stained and the colonies are automatically counted; the results are listed in table 1.

TABLEAU 1

Number of metastatic clonogenic colonies 19 days after inoculation of the tumor cells

| | Lungs |
|---|---|
| NaCl 0.9% | 223 (12-767) |
| CuPRiX (200 mg/kg) | 16.3 (0-44) |

Results expressed as mean and (range), n = 4 or 6

The results obtained show a slowing of tumor growth and also a reduction in the number of metastases in the lungs after treating the mice with $CuPRiX_{30}$. The 4 mice in the control group had metastases in the lungs, while 2 of the 6 treated by CuPRiX had none. No liver metastases were observed in either of the conditions (FIG. 12).

Example 15: Efficacy of the Combination of $CuPRiX_{30}$ and Radiotherapy on Tumor Growth and Survival in a Metastatic Breast Cancer Mouse Model The aim of this example is to show the capacity of $CuPRiX_{30}$ to increase the efficacy of radiotherapy on tumor growth and survival. To this end, 42 8-week-old female BALB/c mice were given a subcutaneous injection of 50 000 4T1 cells (triple-negative breast cancer cells, 50:50 PBS: Matrigel). Ten days after the tumor graft, the mice were randomly split into 4 groups to receive the treatments: the NaCl group (control, n=12), the CuPRiX group (n=10), the NaCl+radiotherapy group (RT, n=9) and the CuPRiX +RT group (n=11).

The mice were given a total of 3 injections of 50 μl of CuPRiX (200 mg/ml) or NaCl (0.9%) spaced apart by 48 h and combined with radiotherapy in fractions of 5×2 Gy (2 Gy per day for 5 days) (FIG. 13). The irradiations took place 1 hour after administration of the treatment, under isoflurane anesthesia.

To monitor tumor evolution and to establish the Kaplan-Meier survival curves, the mice were weighed and the tumors were measured 6 times per week. At the end of the treatment plan, the mice that had reached one of the following limit points for 2 consecutive days were euthanized: loss of 15% of its weight; tumor volume of ≥1000 mm3; persistent ulceration; observation of signs of distress (prostration, rough fur, arched back).

The evolution in tumor volume was calculated as follows: (Tumor volume at time t)/(tumor volume at reference time), where the reference time corresponds to the first day of treatment, i.e. D10. The results obtained show a greater reduction in tumor growth after the treatment combination of CuPRiX+RT than after treatment by RT alone or by CuPRiX alone. The combination of CuPRiX and RT also made it possible to prolong the survival of the animals compared to RT alone (FIG. 14).

INDUSTRIAL APPLICABILITY

The present technical solutions can particularly applied to the field of medicine, in particular for the treatment of tumors.

The present disclosure is not limited to the examples described above, only given by way of example, and it encompasses all the variants that could be envisaged by a person skilled in the art in the context of the protection sought.

The invention claimed is:

1. A method for treating cancer in a patient, the method consisting of steps of:

(a) in vivo capturing copper and/or iron in the patient by administering an effective amount of a colloidal solution of nanoparticles to said patient by intravenous or intratumoral injection, and (b) subjecting the patient to radiotherapy, wherein the nanoparticles act as radiosensitizers, wherein the nanoparticles have the following formula: $[Ch1]_n$—PS—$[Ch2]_m$, wherein:

PS is a polysiloxane matrix,

Ch1 and Ch2 are DOTAGA chelating groups of the following formula (I)

(I)

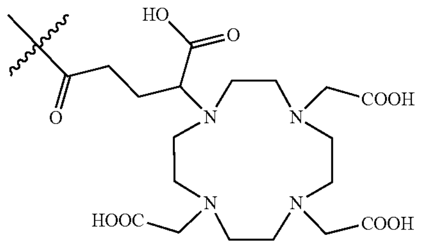

grafted to the polysiloxane matrix by covalent bonding,

Ch1 is uncomplexed,

Ch2 is complexed with a metal cation M2, wherein M2 is the gadolinium cation $Gd^{3+}$, n+m is comprised between 10 and 30, and the mean hydrodynamic diameter is comprised between 2 and 8 nm.

2. The method according to claim 1, wherein n/(n+m) is 20%.

3. The method according to claim 1, wherein n/(n+m) is 30%.

4. The method according to claim 1, wherein when the colloidal solution of nanoparticles is administered by intravenous injection, copper and/or iron is captured in the patient's bloodstream and/or in a tumor environment in the patient.

5. The method according to claim 4, wherein only copper is captured.

6. The method according to claim 1, wherein when the colloidal solution of nanoparticles is administered by intra-tumoral injection, copper and/or iron is captured in a tumor environment in the patient.

7. The method according to claim 1, wherein said colloidal solution is comprised in a pharmaceutical composition further comprising at least one pharmaceutically acceptable excipient.

8. The method according to claim 1, wherein the cancer is a metastatic cancer.

9. The method according to claim 1, wherein treating cancer in said patient comprises reducing tumor growth.

10. The method according to claim 1, wherein the cancer is selected from brain cancers, liver cancers, cancers of the pelvic region, cancers of the upper aerodigestive tract, lung cancers, esophageal cancer, breast cancer, and pancreatic cancer.

11. The method according to claim 10, wherein the cancers of the pelvic regions comprise cervical cancer, prostate cancer, anorectal cancer, and colorectal cancer.

* * * * *